United States Patent
Lin et al.

(10) Patent No.: US 10,401,477 B2
(45) Date of Patent: Sep. 3, 2019

(54) METHOD AND APPARATUS FOR DOPPLER RADAR SIGNAL RECOVERY OF TARGET DISPLACEMENT

(71) Applicant: UNIVERSITY OF FLORIDA RESEARCH FOUNDATION, INC., Gainesville, FL (US)

(72) Inventors: Jenshan Lin, Gainesville, FL (US); Te-yu Kao, Gainesville, FL (US)

(73) Assignee: UNIVERSITY OF FLORIDA RESEARCH FOUNDATION, INC., Gainesville, FL (US)

(*) Notice: Subject to any disclaimer, the term of this patent is extended or adjusted under 35 U.S.C. 154(b) by 399 days.

(21) Appl. No.: 14/631,532

(22) Filed: Feb. 25, 2015

(65) Prior Publication Data

US 2015/0241555 A1    Aug. 27, 2015

Related U.S. Application Data

(60) Provisional application No. 61/944,428, filed on Feb. 25, 2014, provisional application No. 61/949,136, filed on Mar. 6, 2014.

(51) Int. Cl.
*A61B 5/00* (2006.01)
*A61B 5/05* (2006.01)
(Continued)

(52) U.S. Cl.
CPC .............. *G01S 7/41* (2013.01); *A61B 5/024* (2013.01); *A61B 5/0205* (2013.01); *A61B 5/05* (2013.01);
(Continued)

(58) Field of Classification Search
None
See application file for complete search history.

(56) References Cited

U.S. PATENT DOCUMENTS

2008/0300805 A1* 12/2008 Li .................... G01H 9/00
                                                702/56
2010/0198083 A1*  8/2010 Lin .................. A61B 5/05
                                                600/484

OTHER PUBLICATIONS

Cao, Y., et al., "Frequency-Independent Equivalent-Circuit Model for On-Chip Spiral Inductors," *IEEE Journal of Solid-State Circuits*, Mar. 2003, vol. 38, No. 3, pp. 419-426.
(Continued)

*Primary Examiner* — Shaun M Campbell
(74) *Attorney, Agent, or Firm* — Thomas Horstemeyer, LLP

(57) ABSTRACT

Method and apparatus for detecting a movement, such as two or more periodic vibrations, of a target, by sending a radar signal, e.g., near 60 GHz, at the target and processing the signal reflected by the target. One or more components of the movement can have a predominant frequency, such as a frequency of vibration, and two or more components can have different frequencies and, optionally, different magnitudes. A quadrature receiver processes the received signal to produce a base band output signal having in-phase (I) and quadrature-phase (Q) outputs. The in-phase (I) and quadrature-phase (Q) outputs are cross-referenced and real target movement frequency recovered directly in the time domain. System nonlinearity, which does not occur simultaneously on the I and Q channels, is identified and removed. Radar signals having wavelengths near one or more of the target movement magnitudes can be used.

16 Claims, 17 Drawing Sheets

(51) Int. Cl.
  A61B 5/08    (2006.01)
  G01S 7/41    (2006.01)
  A61B 5/024   (2006.01)
  G01S 13/50   (2006.01)
  A61B 5/0205  (2006.01)

(52) U.S. Cl.
  CPC .......... *A61B 5/0816* (2013.01); *A61B 5/7257* (2013.01); *G01S 13/50* (2013.01)

(56) References Cited

OTHER PUBLICATIONS

Cao, C., et al., "Millimeter-Wave Voltage-Controlled Oscillators in 0.13-μm CMOS Technology," *IEEE Journal of Solid-State Circuits*, Jun. 2006, vol. 41, No. 6, pp. 1297-1304.

Chuang, H.R., et al., "60-GHz Millimeter-Wave Life Detection System (MLDS) for Noncontact Human Vital-Sign Monitoring," *IEEE Sensors Journal*, Mar. 2012, vol. 12, No. 3, pp. 602-609.

Dickson, T.O., et a/., "30-100-GHz Inductors and Transformers for Millimeter-Wave (Bi)CMOS Integrated Circuits," IEEE Transactions on Microwave Theory and Techniques, Jan. 2005, vol. 53, No. 1, pp. 123-133.

Droitcour, A.D., et al., "Range Correlation and I/Q Performance Benefits in Single-Chip Silicon Doppler Radars for Noncontact Cardiopulmonary Monitoring," *IEEE Transactions on Microwave Theory and Techniques*, Mar. 2004, vol. 52, No. 3, pp. 838-848.

Jentzsch, A., et al., "Theory and Measurements of Flip-Chip Interconnects for Frequencies up to 100 GHz," *IEEE Transactions on Microwave Theory and Techniques*, May 2001, vol. 49, No. 5, pp. 871-878.

Kao, T.Y., et al., "Design and Analysis of a 60-GHz CMOS Doppler Micro-radar System-in-Package for Vital Sign and Vibration Detection," *IEEE Transactions on Microwave Theory and Techniques*, Mar. 2013, vol. 61, No. 4, pp. 1649-1659.

Kao, T.Y., et al., "A Flip-Chip-Packaged and Fully Integrated 60 GHz CMOS Micro-Radar Sensor for Heartbeat and Mechanical Vibration Detections," *IEEE Radio Frequency Integrated Circuits Symposium*, Jun. 2012, pp. 443-446.

Kim, S., et al., "On the Development of a Multifunction Millimeter-Wave Sensor for Displacement Sensing and Low-Velocity Measurement," *IEEE Transactions on Microwave Theory and Techniques*, Nov. 2004, vol. 52, No. 11, pp. 2503-2512.

Knott, E., *Radar Handbook*, Mc-Graw-Hill, New York, NY, 2008.

Kraemer, M., et al., "Accurate Electromagnetic Simulation and Measurement of Millimeter-wave Inductors in Bulk CMOS Technology," *Proceedings of the 10th Topical Meeting on Silicon Monolithic Integrated Circuits in RF Systems*, Jan. 2010, pp. 61-64.

Kuo, J.L., et al., "A 50 to 70 GHz Power Amplifier Using 90 nm CMOS Technology," *IEEE Microwave and Wireless Components Letters*, Jan. 2009, vol. 19, No. 1, pp. 45-47.

Laskin, E., et al., "Nanoscale CMOS Transceiver Design in the 90-170-GHz Range," *IEEE Transactions on Microwave Theory and Techniques*, Dec. 2009, vol. 57, No. 12, pp. 3477-3490.

Lee, J., et al., "A Low-Power Low-Cost Fully-Integrated 60-GHz Transceiver System With OOK Modulation and On-Board Antenna Assembly," *IEEE Journal of Solid-State Circuits*, Feb. 2010, vol. 45, No. 2,pp. 264-275.

Li, C., et al., "Complex Signal Demodulation and Random Body Movement Cancellation Techniques for Non-contact Vital Sign Detection," *IEEE International Microwave Symposium Digest*, Jun. 2008, pp. 567-570.

Li, C., et al., "Experiment and Spectral Analysis of a Low-Power Ka-Band Heartbeat Detector Measuring From Four Sides of a Human Body," *IEEE Transactions on Microwave Theory and Techniques*, Dec. 2006, vol. 54, No. 12, pp. 4464-4471.

Li, C., et al, "High-Sensitivity Software-Configurable 5.8 GHz Radar Sensor Receiver Chip in 0.13 μm CMOS for Noncontact Vital Sign Detection," *IEEE Transactions on Microwave Theory and Techniques*, May 2010, vol. 58, No. 5, pp. 1410-1419.

Li, C., et al., "Optimal Carrier Frequency of Non-contact Vital Sign Detectors," *Proceedings of IEEE Radio and Wireless Symposium*, Jan. 2007, pp. 281-284.

Liang, C.K., et al., "Systematic Transistor and Inductor Modeling for Millimeter-Wave Design," *IEEE Journal of Solid-State Circuits*, Feb. 2009, vol. 44, No. 2, pp. 450-457.

Lu, H.C., et al., "Flip-Chip-Assembled W-Band CMOS Chip Modules on Ceramic Integrated Passive Device With Transition Compensation for Millimeter-Wave System-in-Package Integration," *IEEE Transactions on Microwave Theory and Techniques*, Mar. 2012, vol. 60, No. 3, pp. 766-777.

Pellerano, S., et al., "A 64 GHz LNA With 15.5 dB Gain and 6.5 dB NF in 90 nm CMOS," *IEEE Journal of Solid-State Circuits*, Jul. 2008, vol. 43, No. 7, pp. 1542-1552.

Petkie, D.T., et al., "Millimeter Wave Radar for Remote Measurement of Vital Signs," *IEEE Radar Conference*, May 2009, pp. 1-3.

Reynolds, S.K., et al., "A Silicon 60-GHz Receiver and Transmitter Chipset for Broadband Communications," *IEEE Journal of Solid-State Circuits*, Dec. 2006, vol. 41, No. 12, pp. 2820-2831.

Yan, W.S.T., et al., "A 900-MHz CMOS Low-Phase-Noise Voltage-Controlled Ring Oscillator," *IEEE Transactions on Circuits and Systems II: Analog and Digital Signal Processing*, Feb. 2001, vol. 48, No. 2, pp. 216-221.

Yan, Y., et al., "Analysis of Detection Methods of RF Vibrometer for Complex Motion Measurement," *IEEE Transactions on Microwave Theory and Techniques*, Dec. 2011, vol. 59, No. 12, pp. 3556-3566.

Yao, T., et al., "Algorithmic Design of Cmos LNAs and PAs for 60-GHz Radio," *IEEE Journal of Solid-State Circuits*, May 2007, vol. 42, No. 5, pp. 1044-1057.

* cited by examiner

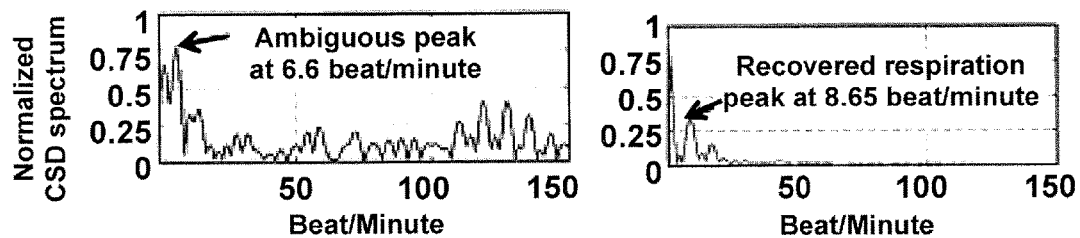
FIG. 18B
FIG. 18C
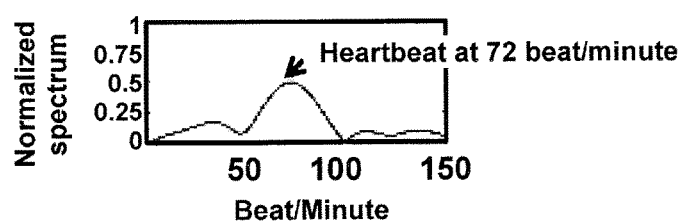
FIG. 18D
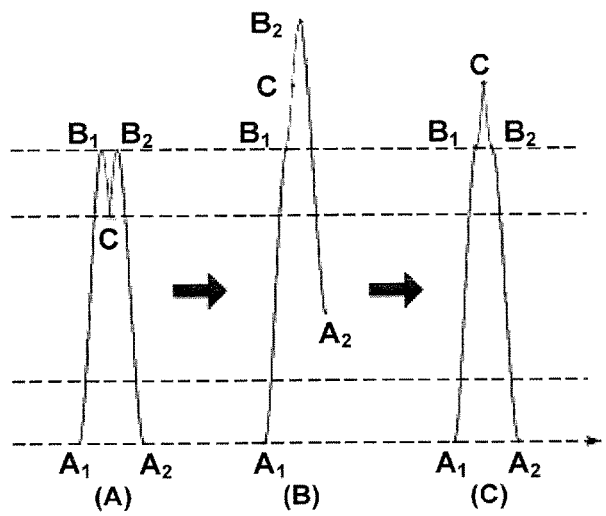
FIG. 19

METHOD AND APPARATUS FOR DOPPLER RADAR SIGNAL RECOVERY OF TARGET DISPLACEMENT

CROSS-REFERENCE TO RELATED APPLICATIONS

The present application claims the benefit of U.S. Provisional Application Ser. No. 61/949,136, filed Mar. 6, 2014, and also claims the benefit of U.S. Provisional Application Ser. No. 61/944,428, filed Feb. 25, 2014, both of which are hereby incorporated by reference herein in their entirety, including any figures, tables, or drawings.

BACKGROUND OF INVENTION

Doppler radar systems operating at Industrial, Scientific, and Medical (ISM) bands near 2.4 GHz, 5.8 GHz, and 24 GHz have been proven to be effective in non-contact vital sign and vibration detection. Recent research has shown the use of higher radar frequencies (shorter wavelength $\lambda$) near 60-GHz ISM band provide a larger system demodulation gain to distinguish small displacements at a longer distance. The use of such higher radar frequencies also helps achieve a highly compact and integrated system, as the antenna size and component sizes are reduced. However, the respiratory chest-wall movement (mr≈1-6 mm) comparable to the wavelength at 60 GHz (5 mm) results in strong nonlinear Doppler phase modulation, which introduces numerous harmonics and inter-modulation peaks on the spectrum. In addition, the heartbeat signal, having an amplitude (mh≈0.2 mm) that is one order of magnitude smaller than that the amplitude of the respiration signal, is usually overwhelmed by the harmonics and noise. Most of the existing analysis on, and techniques for accommodating for, Doppler radar non-linearity is based on Bessel functions and based on the assumption that the target movement is one or more simple sinusoidal movements, and is usually susceptible to system noise and non-ideality.

BRIEF SUMMARY

Embodiments relate to a method and apparatus for detecting a movement of a target. Embodiments can send a radar signal at the target and process the signal reflected by the target to identify the movement. The movement can have one or more components that have a predominant frequency, such as a frequency of vibration. A specific embodiment can use a quadrature receiver to process the received signal to produce a base band output signal having an in-phase (I) and a quadrature-phase (Q) outputs. Embodiments of the subject method can cross-reference the in-phase (I) and quadrature-phase (Q) outputs and recover real target movement frequency directly in the time domain. In embodiments, the system nonlinearity can be identified and removed, as such nonlinearity does not happen simultaneously on the I and Q channels, due to the 90 degree phase shift between the I and Q channels. Embodiments can detect two, or more, periodic movements having different frequencies and, optionally, having different magnitudes. Embodiments of the subject method can provide robust detection of periodic vibrations of a target using Doppler radar. Embodiments can use radar signals having frequencies near 60-GHz, and other frequencies where one or more of the target displacement magnitudes is comparable to the wavelength of the radar signal, $\lambda$. Embodiments can be applied to other wavelength and frequency ranges, including, but not limited to, the wavelength range 0.1-0.3, 0.15-0.25, 0.5-6.5, 1-6, 1-2, 2-3, 3-4, 4-5, 5-6, 6-7, 3-7, 4-6, 4.5-5.5, 4.6-5.4, 4.7-5.3, 4.8-5.2, 4.9-5.1, 4.95-5.05, 4.96-5.04, 4.97-5.03, 4.98-5.02, and/or 4.99-5.01 mm, and/or the frequency range 55-56, 56-57, 57-58, 58-59, 59-60, 60-61, 61-62, 62-63, 63-64, 64-65, 59-61, 58-62, 57-63, 56-64, and/or 55-65 GHz, and applications where the difference between the wavelength of the radar signal and the magnitude of the detected motion is less than ±(0.01, 0.02, 0.03, 0.04, 0.04, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 3.0, 4.0, 5.0, 6.0, 7.0, 8.0, 9.0, 10, 11, 12, 13, 14, 15, 16, 17, 18, 19, and/or 20)%. Embodiments of the subject time-domain recovery method can be applied to arbitrary target displacements, including target displacements occurring in real world situations.

Embodiments of the subject method can be applied to a target located at a distance D from the transmitter and that has a first substantially periodic movement having an amplitude that is at least 80%, at least 90%, at least 95%, at least 100%, and/or greater than or equal to 100% of the $\lambda$ of the radar signal transmitted to and reflected from the target and a second substantially periodic movement having an amplitude that is less than 50%, less than 40%, less than 30%, less than 20%, less than 10%, less than 9%, 8%, 7%, 6%, 5%, 4%, 3%, 2% and/or 1% of the amplitude of the first movement.

BRIEF DESCRIPTION OF DRAWINGS

FIGS. 18A, 18B, and 18C show respiration detection results in (FIG. 18A) the time domain and the complex demodulation signal demodulation (CSD) spectrums (FIG. 18B) before and (FIG. 18C) after the recovery algorithm is applied.

FIG. 18D shows heartbeat rate detected by taking an FFT of successive Follow periods (for example, from t=−6.4 s to t=−4 s) indicated by an embodiment of a recovery algorithm in accordance with an embodiment of the invention.

FIG. 19 shows procedures to realize the continuous Flip and Follow operations in MATLAB® coding (A) Follow segment $A_1$-$B_1$ (B) Flip segments $B_1$-C and C-$B_2$ (C) Follow segment $B_2$-$A_2$.

DETAILED DISCLOSURE

Embodiments of the subject method and apparatus can increase the accuracy of non-contact vital sign and vibration detection when the target displacement is comparable to the radar wavelength. Vital signs that can be detected include a frequency of respiration and a heart rate. Such vital signs can be detected for a human, or an animal that is not a human, such as a dog, a cat, a horse, or other animal. As a result, a 60-GHz Doppler radar system, for example, can be used for healthcare, biomedical sensors, and vibration/security monitoring in various environments. The antenna and component sizes, which are inversely proportional to wavelength, can be greatly reduced by using 60-GHz or higher radar frequencies rather than 2.4 GHz, 5.8 GHz, or 24 GHz systems. In addition, if the radar chip is implemented in a low-cost Complementary Metal-Oxide-Semiconductor (CMOS) process, the radar system including antennas can be easily integrated into popular smartphones and tablet devices. Accordingly, embodiments can be embedded into one of the smartphone functions, for example, making it a pervasive first-aid tool for noncontact vital-sign monitoring or applied to a large sensor network.

The subject signal processing method can allow robust vital sign detection for a person using 60-GHz Doppler radar, and is useful for any other frequencies and detection scenarios where a target displacement amplitude is comparable to the λ of the radar system, such as within 20%, within 15%, within 10%, and/or within 5% of the λ. In a specific embodiment, the magnitude of the periodic movement having the largest magnitude is at least 0.9, at least 0.95, at least 0.96, at least 0.97, at least 0.98, at least 0.99, and/or at least 1 times the λ of the radar signal. Compared to the radar systems using ISM bands near 2.4 GHz, 5.8 GHz, and 24 GHz, the use of higher radar frequencies, such as 60 GHz, greater than 40 GHz, greater than 50 GHz, greater than 60 GHz, and/or greater than 70 GHz provides a larger system demodulation gain to distinguish a small displacement at a longer distance. It also helps reduce integration costs as the antenna and component sizes can be reduced. Most of the existing signal processing for Doppler radar nonlinearity is for frequency ranges lower than 60 GHz and based on frequency-component analysis, which is susceptible to system non-ideality and noise shown on the spectrum. The subject method recovers arbitrary target displacements directly in time-domain, providing a simple but effective solution.

Figure 18A:
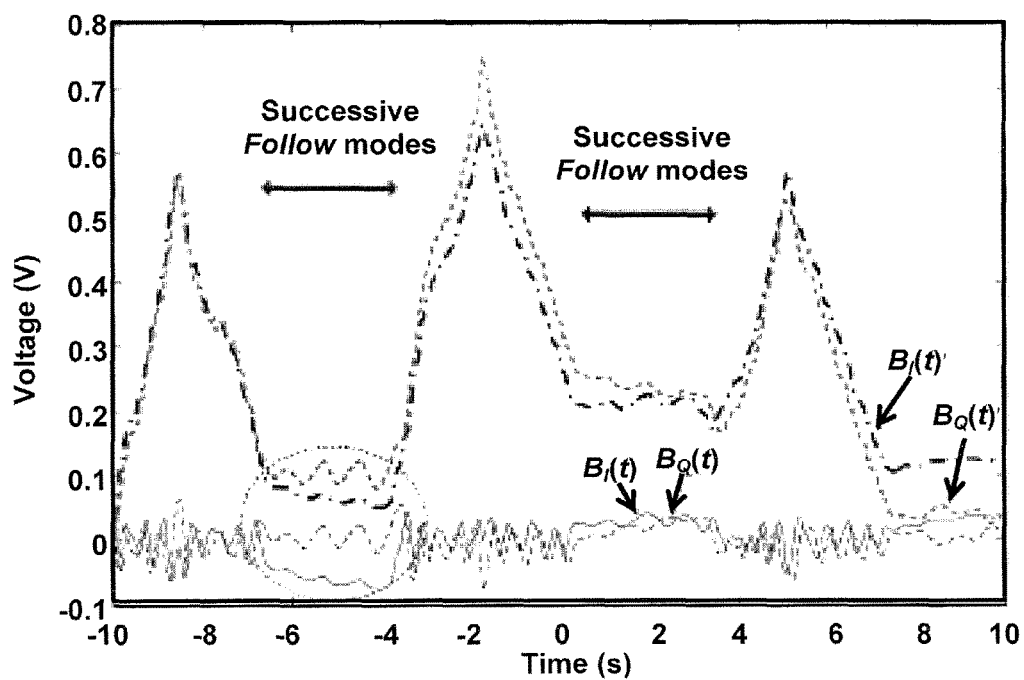

As shown in FIG. 18A, $B_I(t)$ and $B_Q(t)$ show the baseband outputs of a vital sign detection system. The subject breathed normally with inhalation for 2 s, exhalation for 2 s, and interval around 3 s at a distance of 1 m in front of the radar. The respiration rate is 1/(2+2+3)×60=8.57 beat/minute. After Fast Fourier Transform (FFT) is applied to S(t) (=$B_I$(t)+j$B_Q$(t)) in complex signal demodulation, the vital sign spectrum is obtained, as shown in FIG. 18B. In this experiment, both respiration and heartbeat peaks are overwhelmed by the noise and also harmonics due to nonlinear Doppler phase modulation, making the respiration and heartbeat rates ambiguous, and difficult, if not impossible, to distinguish.

Figure 20:
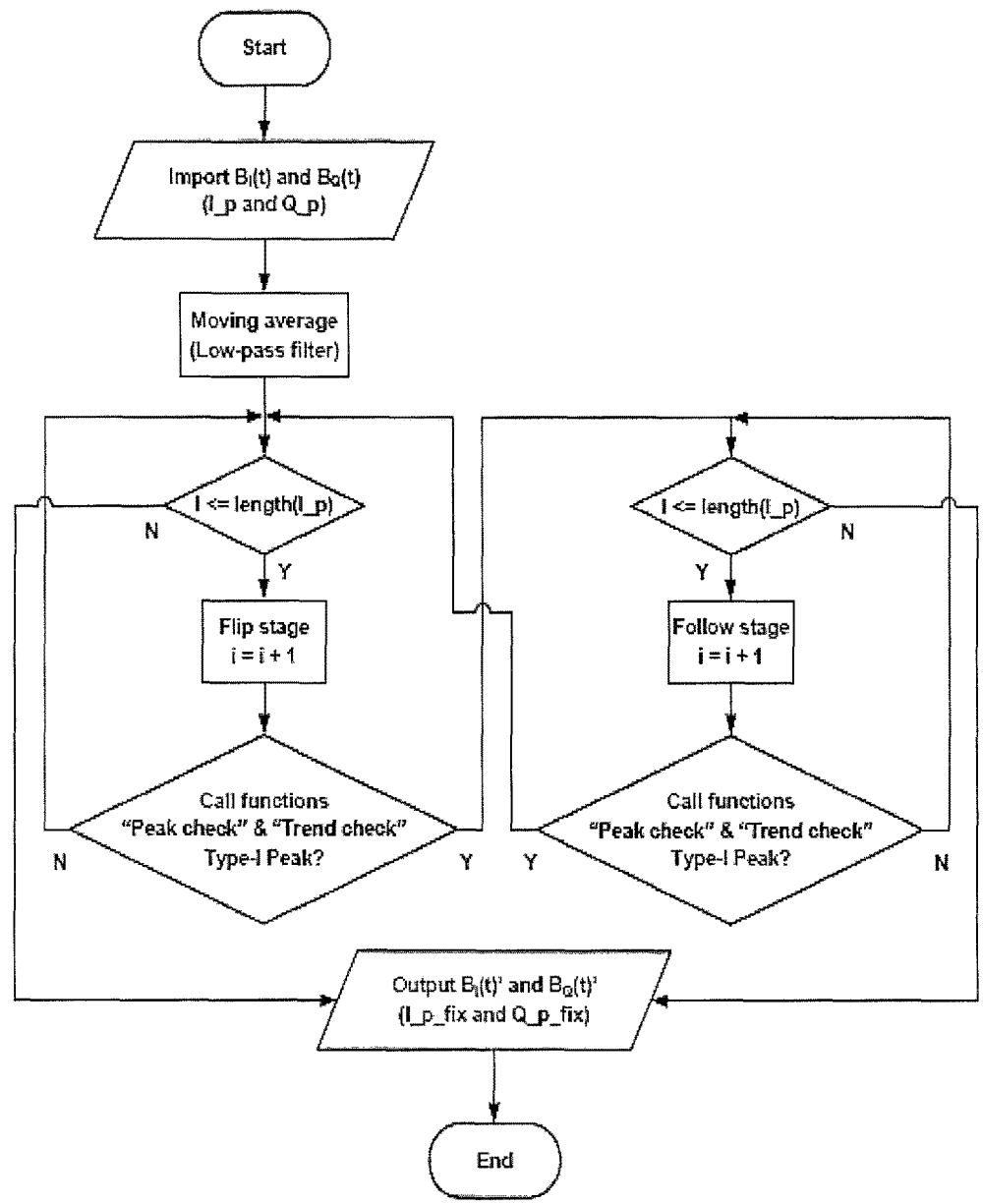
FIG. 20 shows a simplified flow chart of the time-domain recovery algorithm. Similarly $B_I(t)$ and $B_Q(t)$ represents the original waveforms and $B_I(t)'$ and $B_Q(t)'$ are the recovered waveforms. The details of function "Peak check" and function "Trend check" are shown in Appendix.

FIG. 18C shows the spectrum recovered by an embodiment of the subject method using the system implementing the algorithm shown in FIG. 19 and FIG. 20. By simply reading in the quadrature outputs $B_I(t)$ and $B_Q(t)$, the system implementing the algorithm is able recover the human chest-wall movement $B_I(t)'$ and $B_Q(t)'$, and the respiration rate 8.65 beat/minute can be accurately detected. Furthermore, the system implementing the algorithm switches between Flip mode and Follow mode. The heartbeat movement between respirations is captured by "successive Follow modes" as marked in the circle, such that the accurate heartbeat rate 72 beat/minute is successfully extracted by taking a FFT of successive follow mode periods (such as from t=−6.4 s to t=−4 s) in FIG. 18A, and the spectrum is shown in FIG. 18D.

Figure 1A:
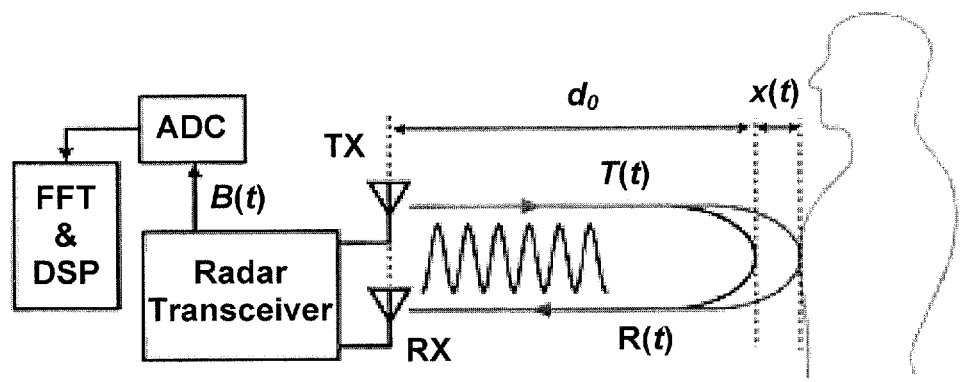
FIG. 1A shows a Doppler radar system which can be utilized in accordance with specific embodiments of the subject invention.

FIG. 1A shows a Doppler radar system for noncontact heartbeat and respiration detection. An un-modulated signal $T(t)=\cos(2\pi ft+\phi_{vco})$ is transmitted to the target, where f and are the frequency and phase noise, and T(t) is reflected from the target and phase modulated by the target displacement x(t). Without considering the amplitude (or power) variation, the baseband output B(t) from the received signal can be expressed as $$B(t) \approx \cos\left(\frac{4\pi x(t)}{\lambda} + \phi_t\right) \quad (1A)$$

where $\lambda$ is wavelength of T(t) and $\phi_t$ is the total residual phase accumulated in the transmission path (i.e., the transmitter signal traveling to the target, being reflected by the target, and the reflected signal traveling from the target to the receiver). In a specific application, x(t) is the human chest-wall movement, which can be modeled as $x(t)=m_r \cdot \sin(2\pi f_r t)+m_h \cdot \sin(2\pi f_h t)$ where $f_r$ and $f_h$ denote the frequency of respiration and heartbeat and $m_r$ and $m_h$ denote the magnitude of respiration and heart rate, respectively. As a quadrature receiver architecture with both I and Q channels is used to solve the null detection point issue, the baseband outputs $B_I(t)$ and $B_Q(t)$ can be expressed as $$B_I(t) \approx \cos\left\{\frac{4\pi x(t)}{\lambda} + \phi_t\right\} = \cos\left\{\frac{4\pi[m_r\sin(2\pi f_r t) + m_h\sin(2\pi f_h t)]}{\lambda} + \phi_t\right\} \quad (1B)$$

$$B_Q(t) \approx \sin\left\{\frac{4\pi x(t)}{\lambda} + \phi_t\right\} = \sin\left\{\frac{4\pi[m_r\sin(2\pi f_r t) + m_h\sin(2\pi f_h t)]}{\lambda} + \phi_t\right\} \quad (1C)$$

As $m_r$ is comparable to or larger than $\lambda$, the modulated phases $4\pi x(t)/\lambda$ in (1B) and (1C) travel through multiples of $2\pi$, so that $B_I(t)$ and $B_Q(t)$ are no longer monotonic during inhale or exhale, as shown in FIG. 18A. This translates to harmonics and intermodulation on the spectrum, which seriously degrades the detection accuracy. Bessel functions can be used to analyze the outputs from frequency-component point of view; however, such analysis is normally limited to sinusoidal target movements and susceptible to system non-ideality and noise.

Figure 16A:
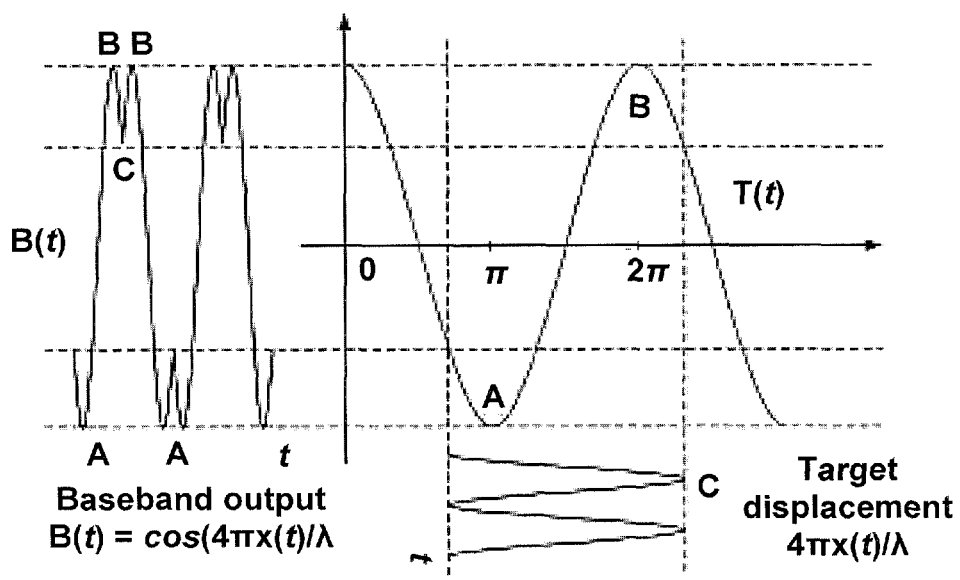
FIG. 16A shows nonlinear input-output mapping when vibration is comparable to or larger than λ.
Figure 16B:
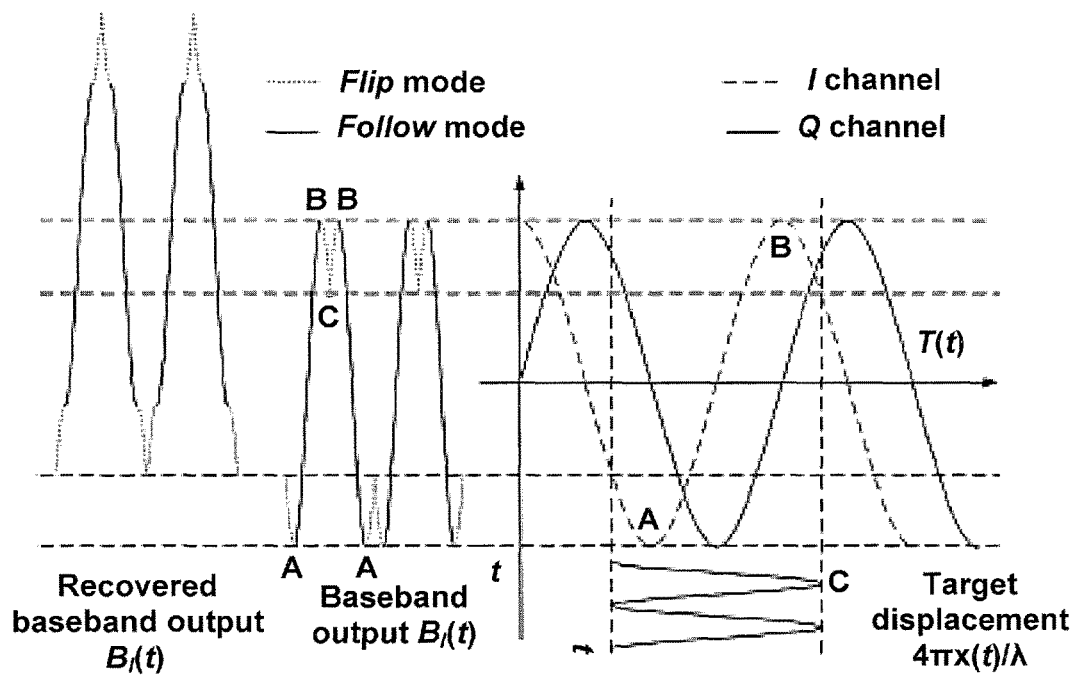
FIG. 16B shows a time-domain recovery algorithm based on I and Q baseband outputs. ($B_Q(t)$ and $B_Q(t)'$ are not shown in the figure.)

Embodiments of the subject method can solve the problem from a time-domain point of view. FIG. 16A illustrates a non-linear input-output mapping that can be utilized in an embodiment of the subject method. Two types of peaks (transition between positive and negative slope) on B(t) can be identified. Type-I peaks (A and B) are due to the distortion of nonlinear system mapping, and Type-II peaks (C) is corresponding to the real target displacement. Plotting both I and Q channels in FIG. 16B, the following relationships can be used to distinguish Type-I and Type-II peaks on $B_I(t)$ and $B_Q(t)$:

1) As a Type-I peak occurs on $B_I(t)$, the slope of $B_I(t)$ changes sign (i.e., positive to negative or negative to positive), while the sign of the slope of $B_Q(t)$ remains unchanged, and as a Type I peak occurs on $B_Q(t)$, the slope of $B_Q(t)$ changes sign, while the sign of the slope of $B_I(t)$ remains unchanged.

2) As a Type-II peak occurs, the sign of the slope of $B_I(t)$ and $B_Q(t)$ change simultaneously. This indicates the peak is due to the original displacement of the target.

3) For any pair of peaks on $B_I(t)$ that are adjacent peaks and are both Type-I peaks (peak A and peak B), the corresponding sign of the slope on $B_Q(t)$ is opposite the sign of the slope for $B_I(t)$, and for any pair of peaks on $B_Q(t)$ that are adjacent peaks and are both Type-I peaks, the corresponding sign of the slope of $B_I(t)$ is opposite to the sign of the slope of $B_Q(t)$.

A recovery algorithm based on the above relationships, in accordance with an embodiment of the subject invention, is implemented in MATLAB®. Other embodiments can implement the non-liner input-output mapping of B(t) to B(t)' via a system incorporating one or more processors that receive B(t) and output B(t)'. By monitoring $B_I(t)$ and $B_Q(t)$, the system implementing the recovery algorithm keeps the non-distorted portion of waveform from the original vibration (in Follow mode) and recovers the distorted portion of waveform (in Flip mode), as demonstrated in FIG. 16B. In specific embodiments, no other intermediate reference signals are used as the system implementing the recovery algorithm converts $B_I(t)$ and $B_Q(t)$ directly to $B_I(t)'$ and $B_Q(t)'$. FIG. 19 illustrates the procedures to perform the continuous Flip and Follow operations in MATLAB® coding. Observed from FIG. 16B, the switch between Flip mode and Follow mode is only triggered by Type-I peaks (peak A and peak B), and these two modes (Flip mode and Follow mode) are always "alternating" regardless of the direction of the displacement x(t). In FIG. 19, (A) shows a section of B(t), and the system implementing the recovery algorithm follows every point in segment $A_1$-$B_1$ and makes no change to the waveform B(t), such as B(t)' is the same as B(t) in segment $A_1$-$B_1$. As soon as the system implementing the recovery algorithm detects peak $B_1$, the system implementing the recovery algorithm vertically flips the next point after $B_1$ (i.e., the first point of segment $B_1$-C after $B_1$) with respect to the value of $B_1$ (i.e., the previous point of segment $B_1$-C) and update all the points of segment $B_1$-C after this current point in a similar manner (i.e., flipping the point with respect to the value of the previous point). In this manner the system implementing the recovery algorithm maintains the continuity of the entire waveform B(t)'. The system implementing the recovery algorithm repeats the same Flip operation point by point in segment $B_1$-C (see (B) in FIG. 19), and then repeats the same flip operation point by point through the last point in segment C-$B_2$ (see (C) in FIG. 19). Since peak C is not a Type-I peak, it does not trigger the switch between Flip and Flow modes. After the system implementing the recovery algorithm detects Type-I peak $B_2$, the system implementing the recovery algorithm switches back to Follow mode from $B_2$ to $A_2$. This embodiment of the subject method eliminates the two Type-I peaks ($B_1$ and $B_2$) generated by the nonlinear system transfer function and, thus, removes the unwanted frequency components.

FIG. 20 presents the simplified flow chart of the time-domain recovery algorithm. In specific embodiments, after importing $B_I(t)$ and $B_Q(t)$, a moving average is applied to remove the glitches of the waveform due to noise and reduce the chance of peak misjudgment, such as missing a peak or falsely detecting a peak. Additional filters can be utilized to improve the recovery accuracy. In the loop, which, in a specific embodiment, goes through every point of the waveform, $B_I(t)$ and $B_Q(t)$ are processed in parallel to increase the efficiency. Specific embodiments can process $B_I(t)$ and $B_Q(t)$ serially rather than in parallel. Function "Peak check" is used to identify any valid peak on the waveform, and function "Trend check" is designed to check if the waveform has a consecutive trend on the waveform (no peak). To prevent false trends the slope=0 case can be eliminated in specific embodiments. The details of the two sub functions, "peak check" and "trend check", are presented in the Appendix. Based on the three relations described earlier to distinguish Type-I and Type-II peaks, once a valid peak is detected on $B_I(t)$ and there is a consecutive trend (no peak) on $B_Q(t)$, the peak is identified as a Type-I peak on $B_I(t)$, which triggers the switch between the Flip and Follow mode on $B_I(t)$ and once a valid peak is detected on $B_Q(t)$ and there is a consecutive trend (no peak) on $B_I(t)$, the peak is identified as a Type-I peak on $B_Q(t)$). The algorithm makes no change to the Type-II peaks, which preserves the original target displacement.

In this way, an embodiment of the method cross-references the outputs from I and Q channels and distinguishes Type-I and Type-II peaks. The ambiguity is resolved by the technique because at a fixed D (distance from the target to the transmitter), the system nonlinearity (Type-I peak) does not happen on both I and Q channels simultaneously due to the 90° phase difference between the I and Q channels. Embodiments of the subject method are suited for radar system with quadrature receiver architecture.

Embodiments also relate to a flip-chip-packaged and fully integrated Doppler micro-radar in 90-nm CMOS for non-contact vital-sign and vibration detection. The use of a smaller wavelength compared with previous works achieves a highly compact system for portable devices, and the radar design considerations at 60 GHz are discussed from both system and circuits points of view. The compact 60-GHz core (0.73 mm) provides a 36-dB peak down-conversion gain and transmits a radar signal around 0 dBm at 55 GHz. Quadrature generation at the intermediate frequency stage of the heterodyne receiver gives a power- and area-efficient solution to the null detection point issue, ensuring robust detection. By using single-patch antennas and without a high-power amplifier, the system demonstrates the first-pass success of human vital-sign detection at 0.3 m. The small mechanical vibration with a displacement of 0.2 mm can be detected up to 2 m away. At 60 GHz, target displacement comparable to wavelength results in strong nonlinear phase modulation and increases detection difficulties.

Microwave Doppler radar has been proved to be effective in noncontact vital-sign sensing and mechanical vibration detections [1]-[4]. Compared with other methods of detection, such as laser-based sensors and interferometers [5], the simple architecture of Doppler radar realized by integrated circuit and system usually makes it a low-power and cost-effective solution. It is also useful in various situations, such as longer distance, low visibility, and through-wall detections [6].

Figure 1B:
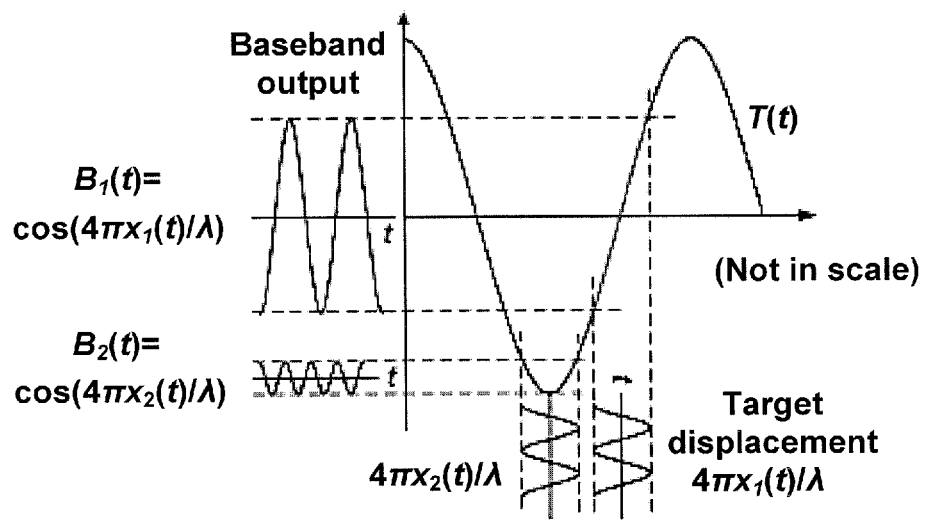
FIG. 1B shows how target displacement modulates the phase of T(t) at $x_1(t)$ (optimal) and $x_2(t)$ (null detection point).

As shown in FIG. 1A, an unmodulated signal $T(t)=\cos(\pi f t + \phi_{VCO})$ is transmitted, where f and $\phi_{VCO}$ are the frequency and phase noise and T(t) is reflected and phase modulated by the target displacement x(t). Without considering the amplitude (or power) variation, the baseband output can be expressed as shown in equation (1A), where $\lambda$ is wavelength of T(t) and $\phi_t$ is the total residual phase accumulated in the transmission path (i.e., the transmitter signal traveling to the target, being reflected by the target, and the reflected signal traveling from the target to the receiver). If $x(t) \gg \lambda$, and $\phi_t$ is odd multiples of $\pi/2$, the system has an approximately linear transfer function near optimal detection points ($B_I(t)$ in FIG. 1B). Near null detection points, the baseband output is smaller and does not contain the fundamental tone of x(t) ($B_2(t)$ in FIG. 1B). The alternating optimal and null detection points occur every $\lambda/8$ as the distance ($d_0$), from the transmitter to the target, varies [2]. In [3], a 5.8-GHz quadrature receiver utilizes I and Q channels with complex signal demodulation (CSD) [7] to eliminate the effect of residual phase. The quadrature architecture allows solving the null detection point issue without extra frequency tuning and achieves robust detection, especially when shorter $\lambda$ is used in the 60-GHz system.

Referring to Equation 1A, for a system at millimeter-wave (mm-wave) frequency range, the shorter $\lambda$ in the denominator provides a higher "system demodulation gain" to distinguish small displacements at a longer distance. A 228-GHz radar system is reported [8] with successful vital-sign detection at 50 m away. Moreover, for a fixed antenna aperture and a flat plate as a radar target, both antenna gain ($G=4\pi A/\lambda^2$) and radar cross section ($\sigma=4\pi T^2_A/\lambda^2$) increase with frequency, where A is the effective antenna area and $T_A$ is the actual area of the plate [9]. Assuming far-field condition for simple analysis, the radar range equation can be approximated as $$P_r = P_t \cdot \sigma \frac{G_t G_r \lambda^2}{(4\pi)^3 R^4} = P_t \frac{A_t A_r T_A^2}{\lambda^4 R^4} \quad (2)$$

where $P_t$ and $P_r$ are the transmitted and received power, and R is the distance. The equation shows apparent advantage of short $\lambda$, if $P_t$, antenna effective areas $A_t$ and $A_r$, and R remain the same and air absorption is negligible in the range of a few meters. For example, $P_r$ at 60 GHz is theoretically $10^2$ times (20 dB) higher than that at 6 GHz, and $\frac{1}{10}$ antenna area is used for both TX and RX.

Increasing the radar frequency poses challenges in circuit implementation and antenna transition. CMOS economies-of-scale with the ability to integrate digital signal processing (DSP) is highly desired, however, performance limitations such as output power, loss, and flicker noise have to be overcome. The research on low-loss, cost-effective antenna transition has drawn increasing attention in the mm-wave ICs, so that a printed circuit board (PCB) antenna with a superior performance compared with the on-chip counterpart can be used. Successful custom packaging [10], [11] horizontally aligns the chip and antenna, which greatly reduces the parasitic inductance. In addition, the bumping and flip-chip process widely used in the IC industry is known to be another promising solution for mm-wave applications. While analysis and optimization have been made based on coplanar-waveguide (CPW)-fed transition [12], [13], a compact flip-chip transition for mm-wave radars, in which TX/RX isolation and optimal local oscillator (LO) distribution path is described.

The radar frequency at 60 GHz is far beyond the optimal carrier frequency for vital-sign detection of a normal person [14], which raises demodulation issues. Typical amplitude of chest-wall movement $m_r$ (1-6 mm) due to respiration is at least one order of magnitude larger than $m_h$ (0.2 mm) due to heartbeat, and the ratio between $m_r$ and $\lambda$ (5 mm) no longer satisfies the small angle approximation used in Equation 1A. The large amplitude difference and strong nonlinear phase modulation [1] significantly increase the complexity of the output spectrum and detection difficulty. A 60-GHz life detection system [15] detects heartbeat by holding the breath to avoid blocking from respiration, and the accuracy of respiration detection itself is limited. Further analysis based on Bessel functions and signal-recovery techniques can be used to detect the vibration comparable to $\lambda$.

II. System Design

Figure 2:
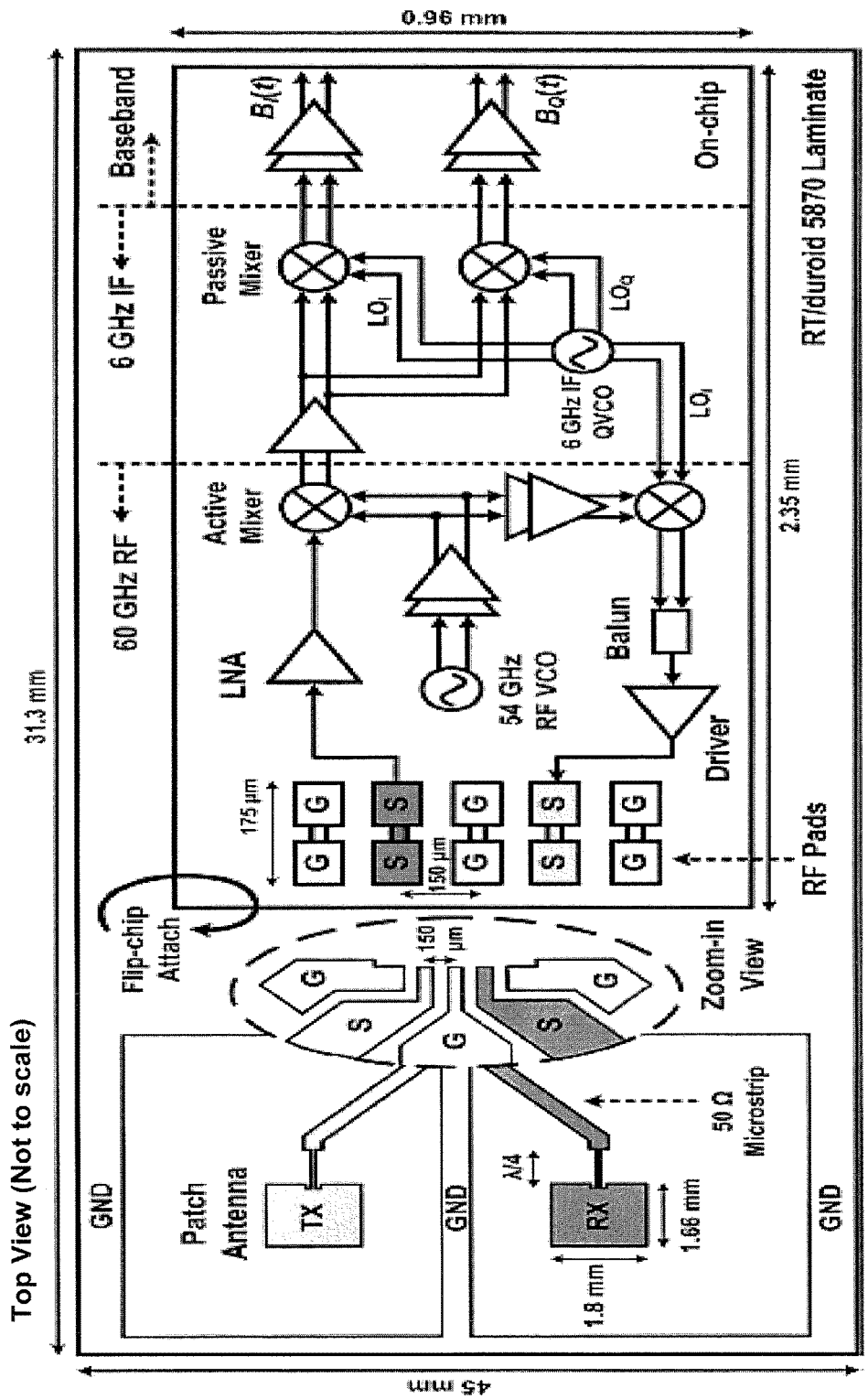
FIG. 2 shows a system block diagram illustrating a CMOS micro-radar, PCB TX and RX patch antennas, and flip-chip integration which can be utilized in accordance with specific embodiments of the subject invention.

The system block diagram illustrated in FIG. 2 is detailed in [16], including the CMOS transceiver chip, patch antennas for TX and RX, and metal traces on the laminate (zoom-in area) designed for flip-chip integration.

Figure 3:
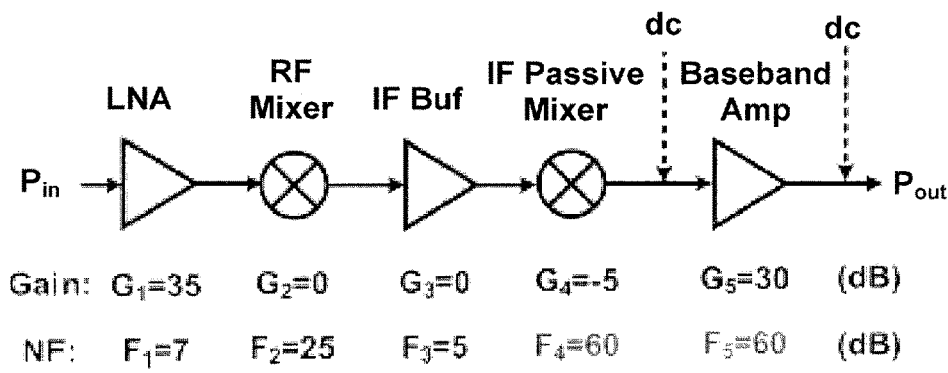
FIG. 3 shows a sensitivity estimation of a radar receiver, where $F_4$ and $F_5$ are estimated to have high noise figure (NF) at 1 Hz due to flicker noise.

Sensitivity estimation provides an idea of margin that certain RX received power is targeted to achieve required output signal-to-noise ratio ($SNR_{re}$). For vital-sign applications, the frequency of interest is near dc (~1 Hz), which results in several situations quite different from typical communication systems. As shown in FIG. 3, the noise figure (NF) $F_4$ and $F_5$ are estimated to be as high as 60 dB [3] due to flicker noise, and total NF is around 31.2 dB even with a high-gain (35 dB) first stage. The fast Fourier transform (FFT) observation time window (TW) at baseband is usually about 20 s to obtain sufficient cycles and maintain good spectrum resolution bandwidth (RBW=1/TW=0.05 Hz). The use of small RBW significantly reduces the overall noise level at output. However, a low sampling frequency ($f_s$) of an analog-to-digital converter (ADC) around 50 Hz is normally chosen to have a reasonable FFT bin size (TW×$f_s$) for real-time computation on portable devices. After sampling, the actual noise level near 1 Hz increases due to aliasing since $f_s$ is far below baseband output bandwidth B (≈1 MHz) and flicker noise corner. Experiment results in [3] shows that the noise level is often dominated by the folded white noise when $f_s$ is low, and the radar RX sensitivity (S) is estimated as (in decibel scale)

$$S = kT \cdot RBW(\text{dB}m) + NF_{wh}(\text{dB}) + \frac{B}{f_s}(\text{dB}) + SNR_{re}(\text{dB}) \quad (3)$$

where kT is thermal noise floor per hertz at input, and $SNR_{re}$ is the requirement at output. Here, kT·RBW (dBm)+$NF_{wh}$ (dB) represents the white noise level before aliasing, and $NF_{wh}$ is around 7.1 dB dominated by the first two stages in FIG. 3. The corresponding sensitivity is −117 dBm at $SNR_{re}$=20 dB. It should be noticed that, if $f_s$ is increased or RX has a higher flicker noise corner, the folded flicker noise might become dominant and degrade the sensitivity.

The estimation of radar received power is nontrivial since it involves a radar cross section of the human body, and sometimes the short range results in near-field detection where (2) is invalid. However, the maximum possible received power can be estimated by assuming an infinite perfect reflector and $$P_r = P_t + G_t + G_r + 20 \cdot \log\left(\frac{\lambda}{4\pi R}\right) \quad (4)$$

where $G_t$ and $G_r$ are both 5 dB, $P_t$ is set at 0 dBm, and the target is 2 m away. The maximum received power $P_r$ is then calculated to be 70 dBm at 60 GHz while the travel distance R is 4 m based on the image theory. In the real case, the received power is lower since the actual target has a smaller reflection area and other sources of loss are present. The estimation above reveals possible margin between the received power and sensitivity, and it indicates the need for a high-gain low-noise amplifier (LNA) for noise suppression and minimized flicker noise of baseband circuit blocks.

For the detection within a few meters, moderate transmitted power around 0 dBm in (4) is targeted to reduce TX power consumption, as long as the received power meets the sensitivity requirement. Gain stages may be placed at RX to satisfy ADC input specifications. In fact, a Doppler radar transmitting unmodulated radar signal allows TX operating in nonlinear region to have high efficiency. For comparison, generally, one stage of an LNA in 90-nm CMOS achieves a gain around 7 dB with a power consumption less than 15 mWat 60 GHz [17], [18]. However, state-of-the-art power amplifiers (PAs) achieving 20-dB gain and 10-dBm saturated power ($P_{sat}$) usually require more than 150 mW [19]. Thus, a TX driver amplifier operating near is adopted in the system for the short-range detection.

A quadrature receiver is required for complex signal demodulation (CSD) to eliminate the null detection points. I/Q separation is realized at the IF stage of the heterodyne receiver instead of a direct-conversion topology, which avoids the loss, mismatch, and power consumption of 60-GHz I/Q separation and distribution. Because the phase noise is correlated at short detection range and significantly reduced by range correlation effect [2], a compact free-running quadrature ring voltage-controlled oscillator (VCO) can be used at IF to drive two passive mixers with large transistor size. The large passive mixers are used for low flicker noise, because this noise from mixer is not cancelled through range correlation. The wide tunable IF provided by the ring VCO compensates the possible RF drift due to mm-wave circuit modeling uncertainty and improves the system robustness. In addition, the IF frequency chosen roughly a decade away from the RF LO (54 GHz) makes the LO feed-through be effectively attenuated by the output tank of the RF mixer.

For the system floorplan shown in FIG. 2, single-ended TX and RX antennas are used and placed closely on the same side of the chip to minimize loss and power consumption of 54-GHz LO distribution, and it prevents the dc/baseband connections from interfering with antennas. The proposed G-S-G-S-G transition achieves impedance match and provides sufficient TX/RX isolation to reduce the direct coupling of signal from TX. By using the 150-μm pitch and 50-Ω impedance interface, on-wafer (for chip) and on-board (for antennas) probing measurements can be conducted separately. The antennas and flip-chip transition were designed at the measured optimal operating frequency of the chip after fabrication.

III. Circuit Component Design

A. Radar Receiver Front-End

Compact lumped-element-modeled inductors instead of transmission lines are extensively used throughout the 60-GHz front-end. Mechanisms such as skin and proximity effects, loss, and return current path [20] were captured by 3-D electromagnetic (EM) simulation to increase the effective quality factor (Q) [21]. In the 90-nm process, inductors on the top metal layer (M9) are surrounded by thick chip ground (GND) walls stacking from the substrate all the way to M9, minimizing GND resistance and inductance. Removal of GND underneath the inductor reduces the parasitic capacitance ($C_p$) and improves Q. Increasing the number of turns achieves the same inductance with smaller footprint and thus $C_p$ as listed in Table I. However, the series resistance ($R_s$) of a two-turn inductor is higher than that of the one-turn inductor, which is largely due to the current crowding effect at high frequencies [22]. Thus, the one-turn inductor has better, despite the increase in area and $C_p$. Considering the tradeoff between area and Q, for example, inductor $L_{d1}$ in FIG. 4 was realized by a 1.5-turn structure to provide 95-pH inductance at 60 GHz.

TABLE I

SIMULATED INDUCTOR PERFORMANCE AT 60 GHz

| Number of Turns[a] | Inductance (nH) | $C_p$ (fF) | $R_s$ (Ω) | Q |
|---|---|---|---|---|
| 1 | 124.2 | 17.2 | 1.7 | 18.6 |
| 2 | 122.1 | 10.4 | 2.4 | 15.7 |

[a] 3-μm trace width and 2-μm trace spacing in UMC 90-nm CMOS process with nine metal layers.

Figure 4A:
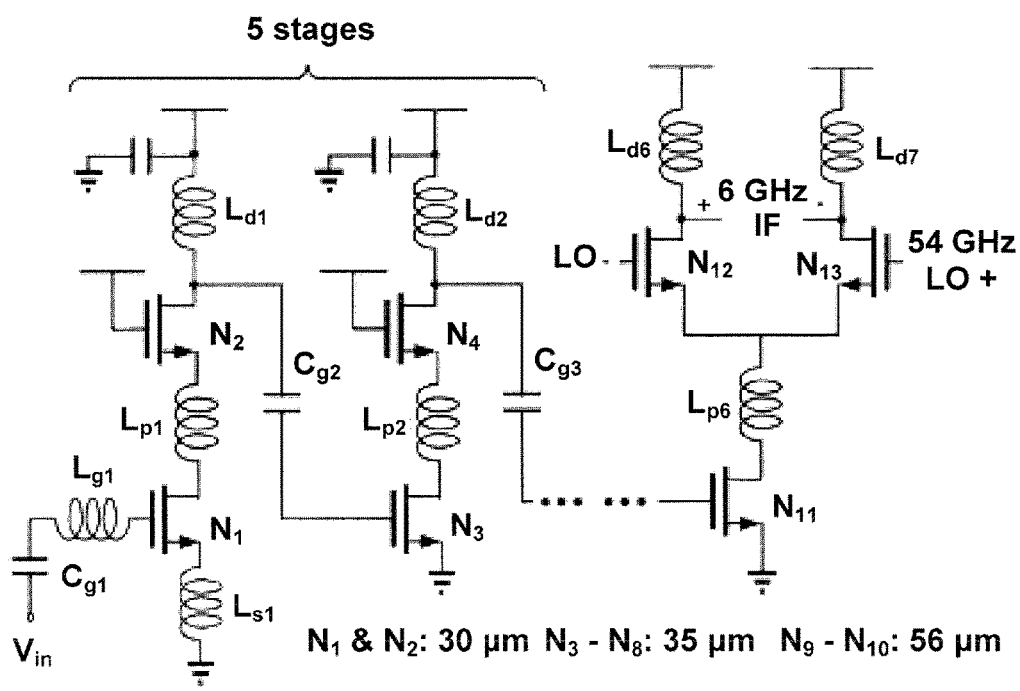
FIG. 4A shows a RX front-end (60 to 6 GHz), including the five-stage LNA, single-ended mixer, and 54-GHz VCO (bias and VCO details not shown) which can be utilized in accordance with specific embodiments of the subject invention.
Figure 4B:
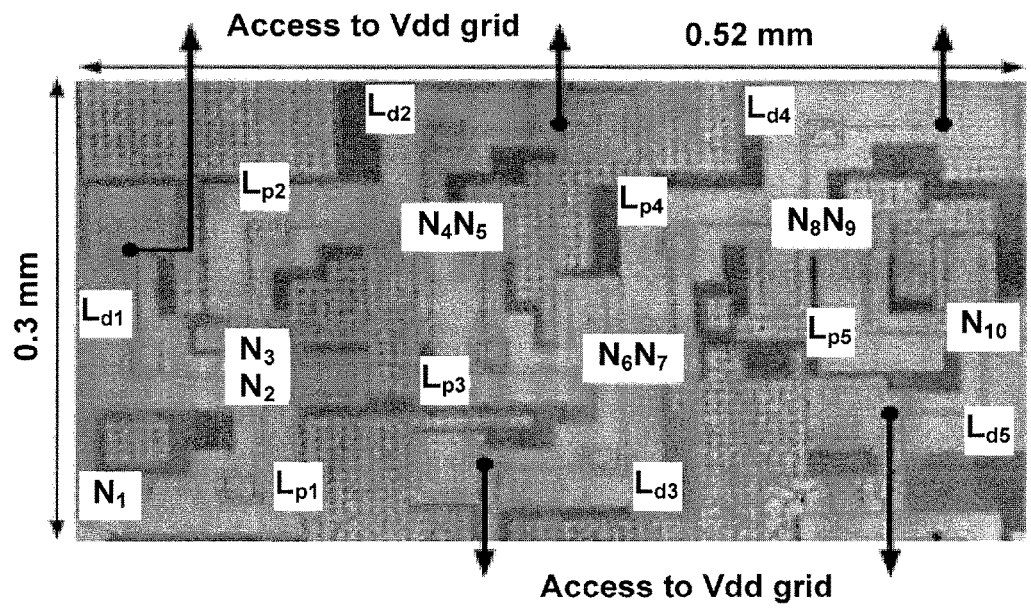
FIG. 4B shows a microphotograph showing the cascade portion of a LNA layout and vertical access to a power grid which can be utilized in accordance with specific embodiments of the subject invention.

Analysis in Section II indicates the need for a high-gain LNA in the RX front-end. As illustrated in FIG. 4A, the input of LNA ($V_{in}$) is from the single-ended patch antenna through flip-chip transition. Transistors are biased at the current density around 0.2 mA/μm for the $f_{max}$ and noise performance [17], and extra parasitic capacitance across the gate, drain, and source due to interconnects was estimated by a three-port extraction in the 3-D EM simulator [23] and included in the circuit simulation. The cascode topology with series inductor ($L_{p1}$-$L_{p5}$) is chosen to improve the gain and noise [17]. As presented in FIG. 4B, the 1.5-turn, L-shaped inductors can be arranged to achieve a highly compact layout at a low coupling level between adjacent inductors. Simulation shows that the LNA provides a 38-dB gain and 5.2-dB NF at 60 GHz while consuming 38 mA at a 1.2-V power supply.

The single-balanced mixer with inductive loads ($L_{d6}$=$L_{d7}$=3.4 nH) serves as a single-ended to differential conversion for the following mixers. It shows a gain of 0 dB, and the 54-GHz LO feed-through is greatly attenuated by the resonant tank at IF. Similar to methods in [24], a 54-GHz LC cross-coupled VCO tuned by accumulation-mode varactors is implemented to drive up- and down-conversion mixers. The simulated phase noise is −101 dBc/Hz (1-MHz offset) at 54 GHz, and the tuning range covers from 51.6 to 54.9 GHz. The first stage of the LO distribution buffers utilizes cascade topology to isolate the core, and common-source (CS) is used in the rest of the LO buffers for the larger voltage headroom, avoiding the pole of cascode transistors. At the power consumption of 110 mW, the receiver front-end provides conversion gain of 38 dB with one of the IF outputs terminated by 50Ω. Simulated input 1-dB compression point ($P_{1\ dB}$) is at −44 dBm which is much higher than the radar received power estimated in (4).

B. Radar Transmitter Front-End

Figure 5A:
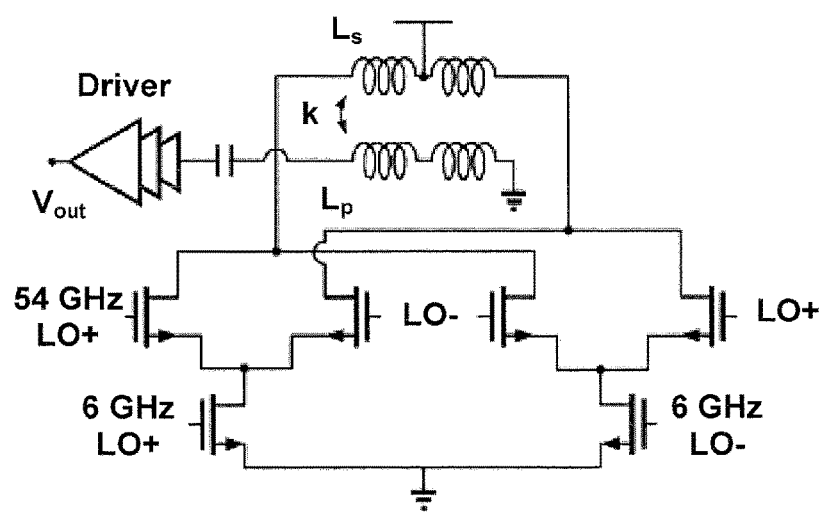
FIG. 5A shows a TX front-end (6 to 60 GHz) using a double-balanced mixer, balanced loads (balun), and three-stage driver which can be utilized in accordance with specific embodiments of the subject invention.
Figure 5B:
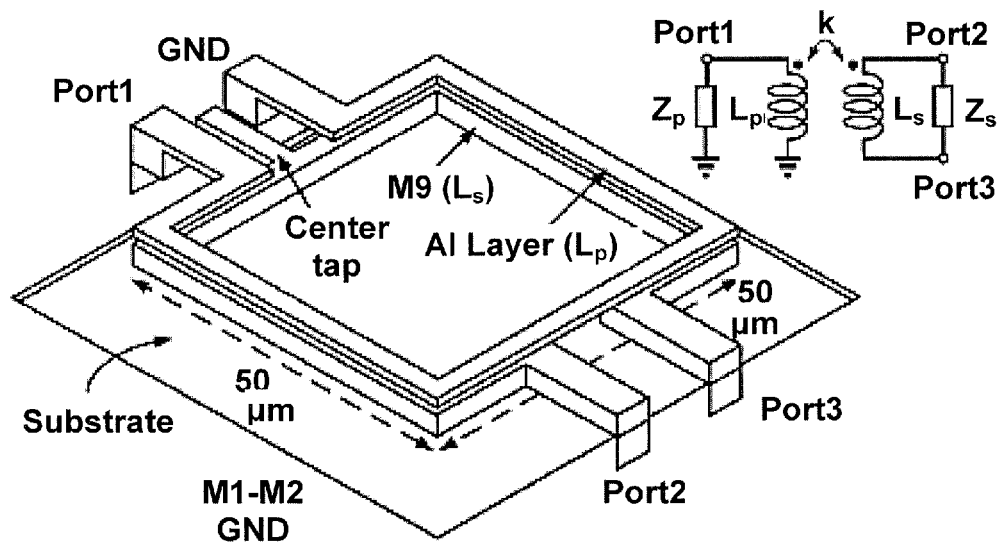
FIG. 5B shows a compact lumped-element-modeled coupled-inductor balun for differential to single-ended conversion which can be utilized in accordance with specific embodiments of the subject invention.

The TX shares the same VCOs with RX to utilize range correlation effect in the radar system. FIG. 5A shows the front-end converting differential LOs to a single-ended RF output for the TX antenna. The compact balun in FIG. 5B realized by coupled inductors provides balanced loads for the mixer while minimizing the area overhead. Based on the CMOS metal design rules, the vertically stacked transformer has less magnetic flux leakage and higher coupling coefficient (k) compared with that of a planar transformer, and the GND plane underneath was removed similar to that in inductor design. Considering the area and parasitic loss, $L_p$ and $L_s$ were designed at 108 and 88.5 pH, respectively. The transformer can be represented as two coupled inductor models, and the value of k is around 0.65. The impedance transformation follows $Z_s/Z_p=L_s/L_p=n^2$, where n is the turn ratio. In 3-D EM simulation, the differential to single-ended insertion loss of the balun is approximately 5 dB at 60 GHz, which is dominated by the limited mutual inductance. Multiturn inductors may be used to improve k at the cost of higher parasitic loss.

The three-stage TX driver uses two cascode stages and a CS-tuned amplifier as the last stage. In the simulation, the output of 6-GHz LOs from the IF ring VCO at −10.7 dBm (differential) is up-converted to 60 GHz with the power level boosted to 2 dBm (single-ended) by the driver, which operates near its $P_{sat}$. The conversion gain from IF to RF is 12.7 dB, and the driver output is matched to 50Ω for the flip-chip transition and antenna. Overall, the TX front-end consumes 35 mW of power and 0.13-mm² area, which are both less than 10% of the overall system consumption.

C. IF VCOs and Passive Mixers

Figure 6A:
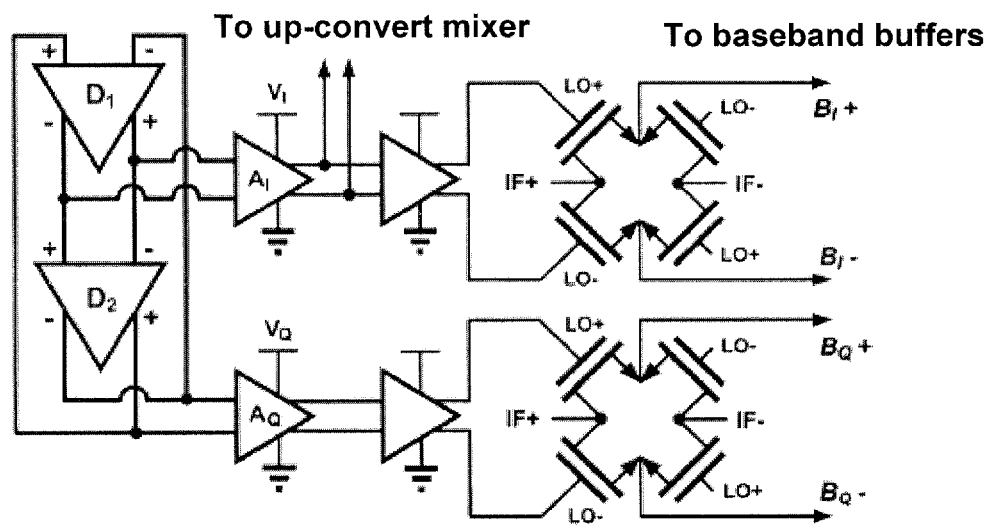
FIG. 6A shows IF stages (6 GHz to dc), including a quadrature ring VCO, LO buffers, and passive mixers which can be utilized in accordance with specific embodiments of the subject invention.
Figure 6B:
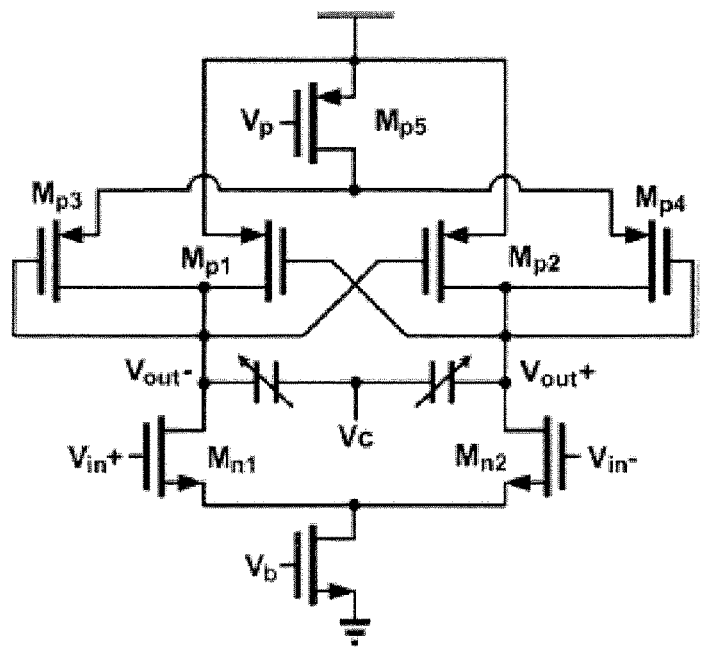
FIG. 6B shows a design of a delay cell (D1 and D2) which can be utilized in accordance with specific embodiments of the subject invention.

As shown in FIG. 6A, the two-stage ring VCO outputs four phases (0°, 90°, 180°, and 270°) based on Barkhausen criteria. The differential I and Q LOs with two-stage resistive-load buffers are able to drive large passive mixers, while I LO signals are also needed by the up-converted mixer. The buffers ($A_I$ and $A_Q$) have separate power supply ($V_I$ and $V_Q$) to compensate for possible amplitude mismatch due to the different loads. The two passive mixers with large transistor sizes (75 μm) avoid transconductor stage and dc bias current to minimize the flicker noise at the baseband outputs [3]. FIG. 6B shows the design of the delay cell ($D_1$ and $D_2$), which includes two tuning mechanisms to improve the precision and tuning range. By only looking into the left-hand side of the delay cell, the oscillation frequency can be represented as [25]

$$f_{os} = \frac{1}{2\pi}\sqrt{\frac{g_{mn1}^2 - (G_L - g_{mp1} + g_{mp3})^2}{C_L^2}} \quad (5)$$

where $g_m$ is the transconductance of the transistor, $G_L$ stands for the total resistive load of $M_{n1}$, $M_{p1}$, and $M_{p3}$, and $C_L$ is the total capacitance seen at the output node ($V_{out-}$). By controlling $V_P$, turning on $M_{p3}$ achieves the highest $C_L(G_L + g_{mp3}=g_{mp1})$ at a fix $C_L$, while turning off $M_{p3}$ results in the lowest $f_{os}$. The accumulation-mode varactors at output nodes provide extra flexibility to tune $C_L$ at the cost of reduced maximum $C_L$. The width ($W_V$) and number of finger ($F_V$) are chosen to be the minimum allowed by the process ($W_V$=1.6 μm, $F_V$=4) to reduce the impact on highest $f_{os}$, and the channel length ($L_V$) is set to be maximum ($L_V$=2 μm) to achieve highest tuning range. The simulated tuning range is 63% (5.2-9.96 GHz) without the varactors and increased to 89% (3.28-8.5 GHz) by adding them. The phase noise is −83 dBc/Hz (1-MHz offset) at $f_{os}$=6.4 GHz, and total power consumption of the IF stage is 99 mW.

D. Flip-Chip Transition and Antenna

Figure 7:
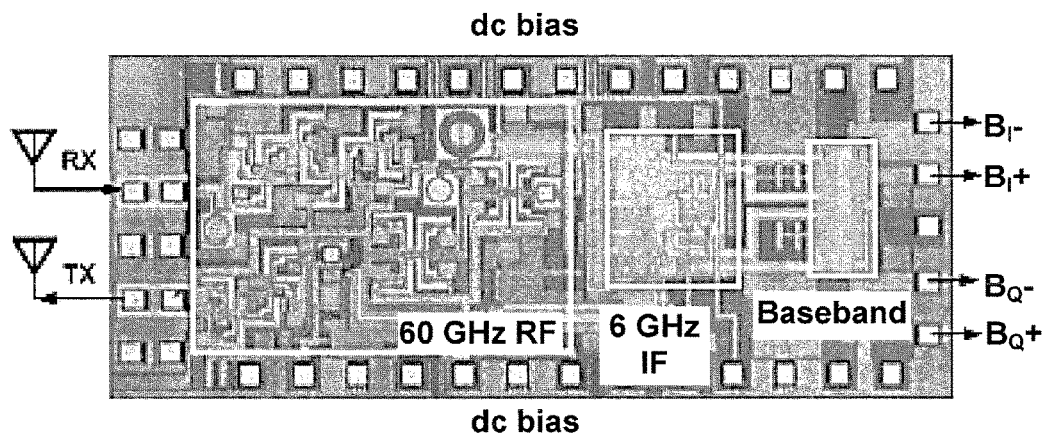
FIG. 7 shows a microphotograph of a 60-GHz CMOS radar chip which can be utilized in accordance with specific embodiments of the subject invention.
Figure 8:
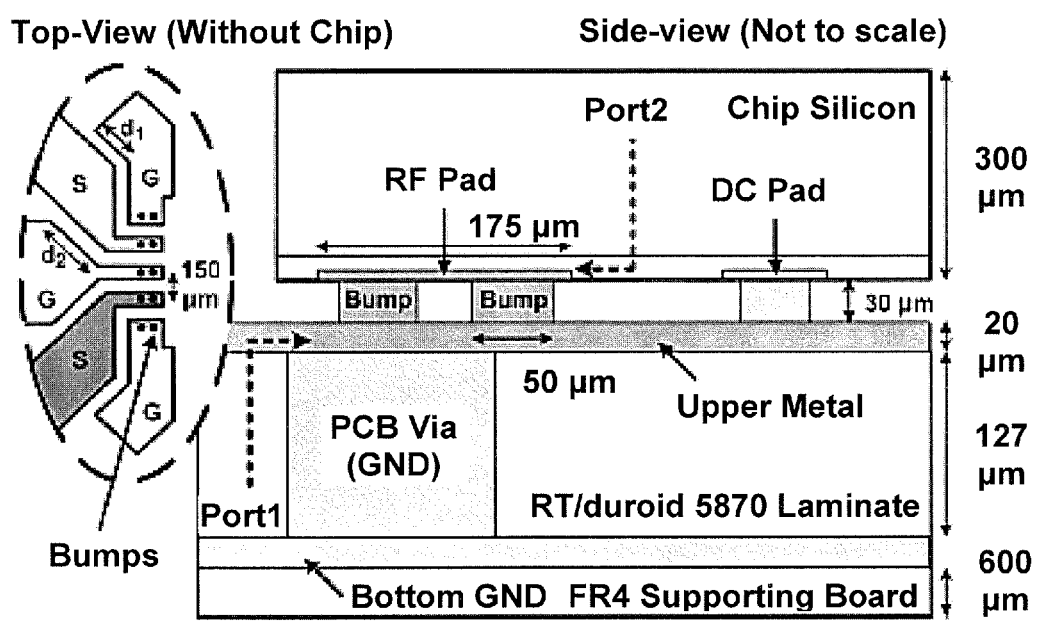
FIG. 8 shows a top view and side view of a flip-chip transition design which can be utilized in accordance with specific embodiments of the subject invention.
Figure 9A:
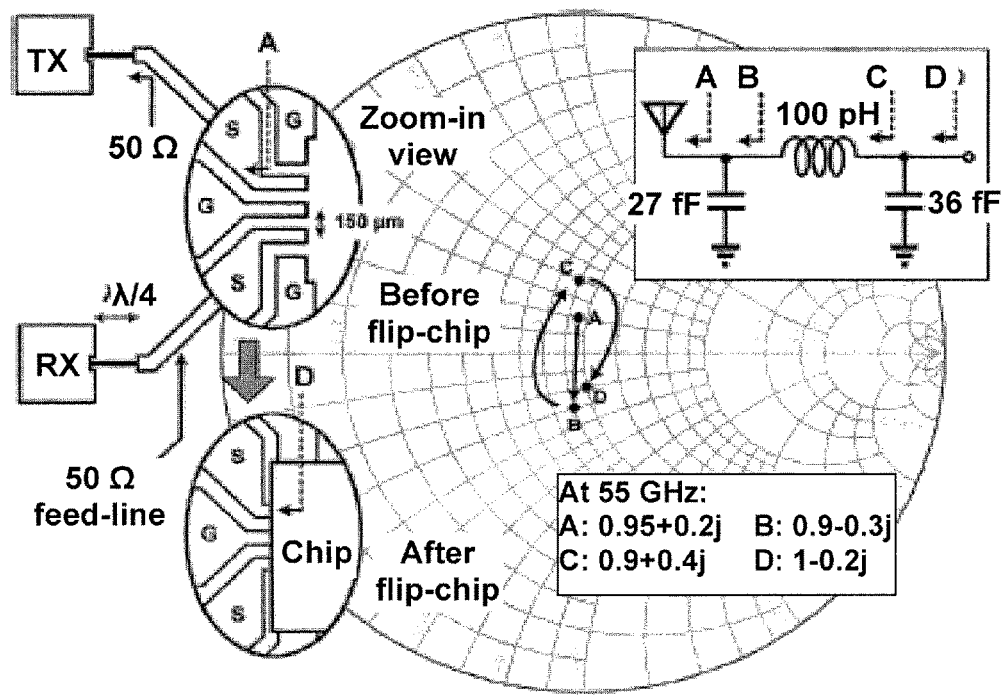
FIG. 9A shows impedance transformation at 55 GHz before and after flip-chip process which can be utilized in accordance with specific embodiments of the subject invention.

The flip-chip transition and antennas were designed at the optimal operating frequency (55 GHz) of the transceiver circuits measured in Section IV. The radar transceiver chip shown in FIG. 7 was flipped on the PCB structure, as presented in FIG. 8. A very thin layer of RT/duroid 5870 high-frequency laminate was chosen to maintain small width of 50-Ω lines and reduce spurious radiation, and a thick FR4 substrate underneath is used to support the soft RT/duroid substrate. In the top view, G-S-G-S-G traces on PCB provide an impedance-matched transition between the wide PCB 50-Ω lines and small on-chip RF pads. The increased inductance due to the taper structure is capacitively compensated by controlling the length $d_1$ and $d_2$. The flip-chip transition can be modeled as a two-port network where the series inductance and shunt capacitance to GND is extracted from 3-D EM simulation. By using two solder bumps in parallel and proper dimensions of PCB traces, bumps, and on-chip pads, the two-port network maintains the impedance match around the center of the Smith chart as seen in FIG. 9A. The insertion loss of the transition is estimated to be 1.5 dB at 55 GHz. As demonstrated in the flip-chip design, the series inductance is no longer dominant and it is sufficiently small to be compensated by the shunt capacitance to maintain adequate matching. The series resistance of the transition is also negligible.

Figure 9B:
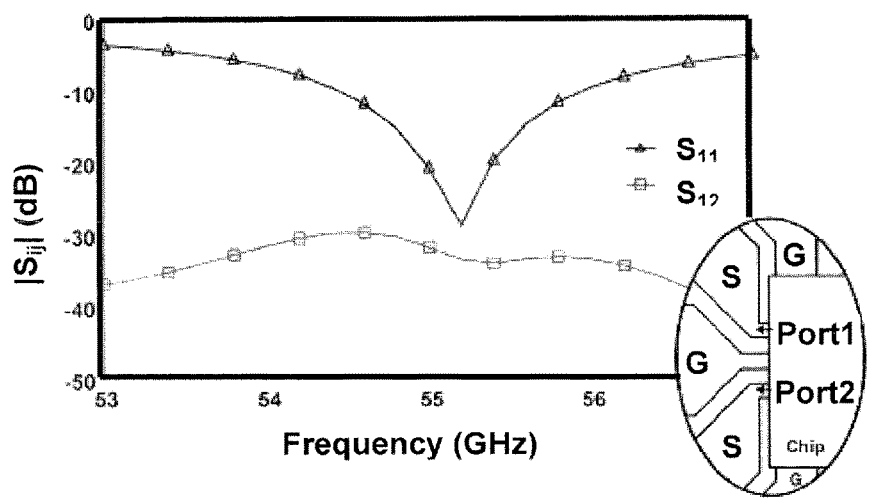
FIG. 9B shows simulated final TX and RX patch antennas S-parameters at point D which can be utilized in accordance with specific embodiments of the subject invention.

The use of thin laminate limits the antenna bandwidth; however, for the single-tone radar signal, it works like a high-Q band-pass filter to reject unwanted frequencies. Orthogonal 50-Ω feed-lines on PCB reduces magnetic coupling between TX and RX, and the single patch antenna shows a peak gain of 4.86 dBi in the measurement. FIG. 9B presents the final S-parameters of the antennas after flip-chip process. In the simulation, port 1 (TX) and port 2 (RX) are placed on the chip and $S_{12}(\approx-34$ dB) shows the isolation.

IV. Experiments and Analysis

A. Circuit Blocks Measurement

Figure 10A:
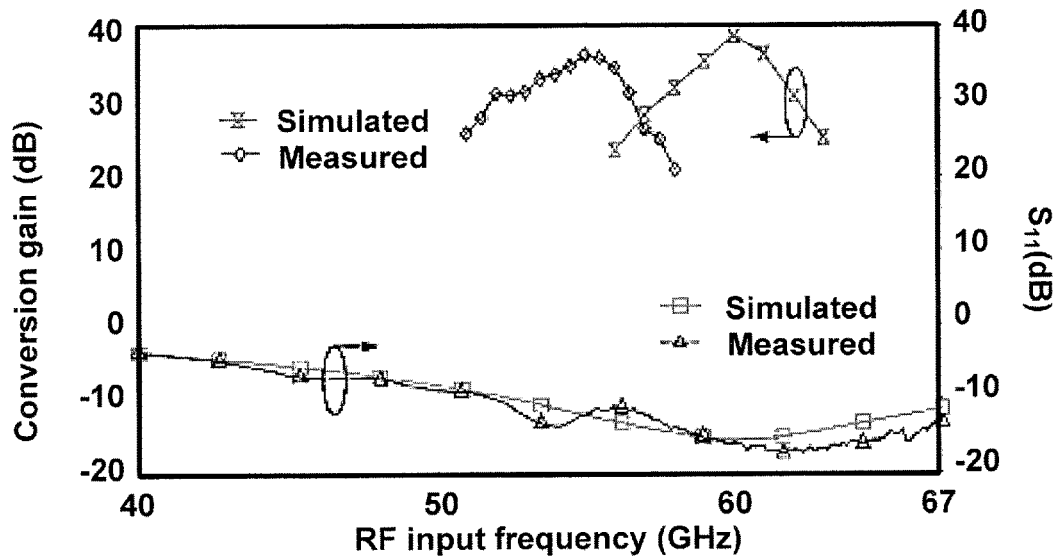
FIG. 10A shows measured RX down-conversion (60 to 6 GHz) gain versus RF frequency, where the RF input power was set at −60 dBm.
Figure 10B:
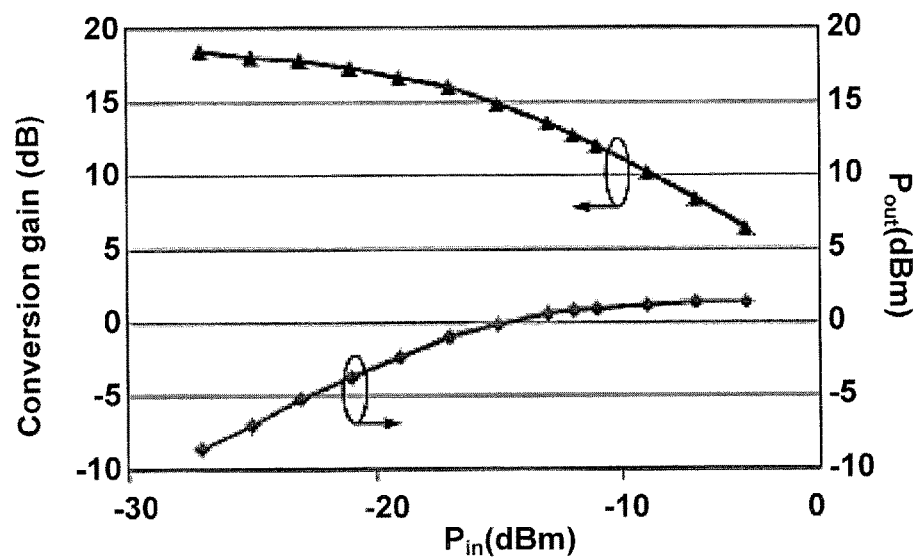
FIG. 10B shows measured TX up-conversion (6 to 60 GHz) gain compression and $P_{in}$ (differential) versus $P_{out}$ (single-ended).

A separate test structure of the 60-GHz transceiver front-end was measured on-wafer. As plotted in FIG. 10A, the peak down-conversion gain is 36 dB from RF to IF (single-ended) with the RF VCO operating at 48.4 GHz. The tuning range of the RF VCO is from 48 to 51 GHz. In the first pass, the reduced peak gain and shifted frequency from 60 to 55 GHz are possibly due to modeling inaccuracy and underestimation of parasitics. The measured input $P_{1\,dB}$ of the receiver is −42 dBm. FIG. 10B shows the measurement results of TX front-end. As the IF input is fixed at 6.6 GHz and RF VCO at 48.4 GHz, the output $P_{1\,dB}$ and $P_{sat}$ are 0.3 and 1.5 dBm at 55 GHz. In this test structure, an extra on-chip balun was used to convert the single-ended IF input to differential signal for the up-converted mixer, and the simulated balun loss was de-embedded. As the IF VCO power is estimated to be −10 dBm (differential), the radar TX output power reaches 1 dBm, which is very close to as previously anticipated. The total power consumption of the transceiver front-end is 190 mW at 1.2 V power supply.

Figure 11:
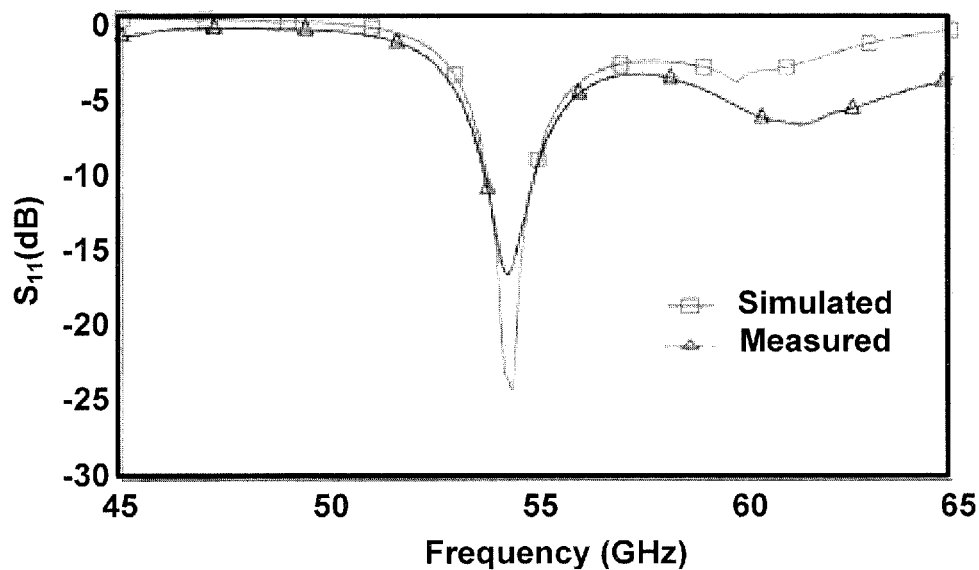
FIG. 11 shows simulated and measured $S_{11}$ of the PCB patch antenna.

FIG. 11 shows the measured $S_{11}$ of the patch antenna before flip-chip process similar to point A in FIG. 9A. The good agreement between simulation and measurement indicates the feasibility to design the antennas right at the measured optimal frequency of the transceiver chip, even the antenna bandwidth is limited by the thin PCB structure.

B. Mechanical Vibration and Heartbeat Detection

Figure 12:
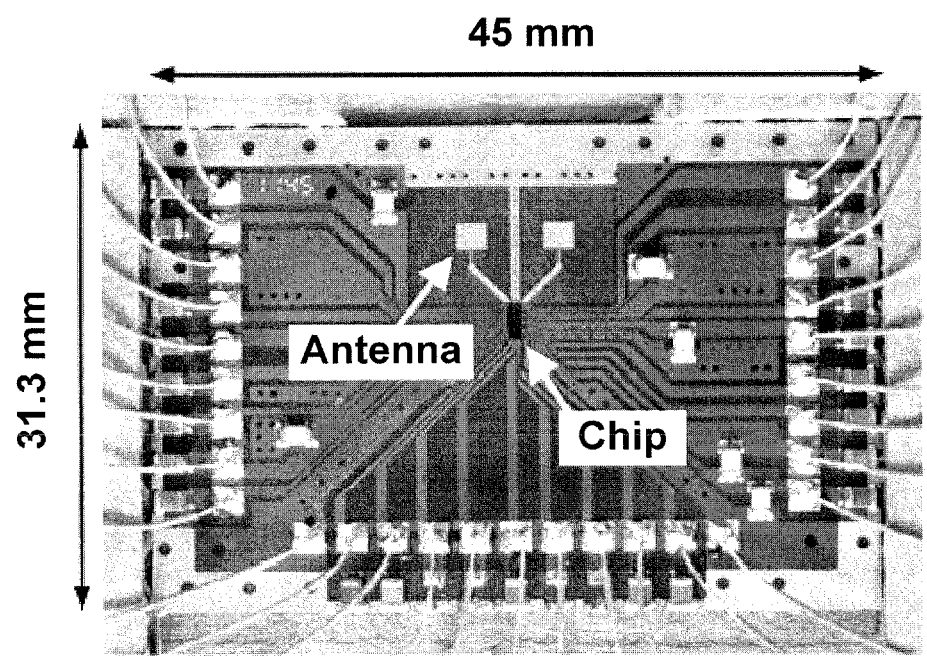
FIG. 12 shows a final system photograph including the flipped chip, TX and RX patch antennas, bypass capacitors, and bias through dc wires which can be utilized in accordance with specific embodiments of the subject invention.
Figure 13A:
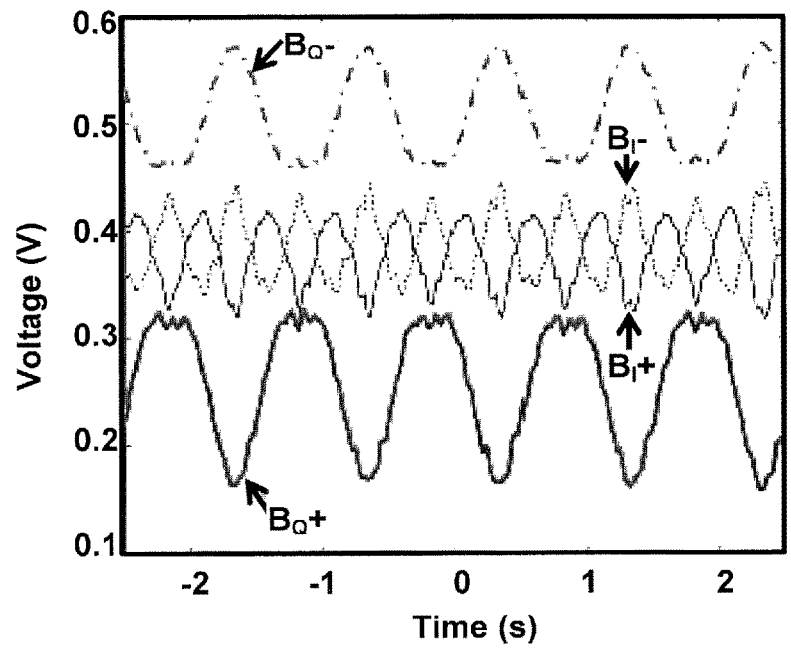
FIGS. 13A and 13B show I and Q baseband outputs of 1-Hz vibration detection as (FIG. 13A) Q at optimal and I at null detection point and (FIG. 13B) I at optimal and Q at null detection point.
Figure 13B:
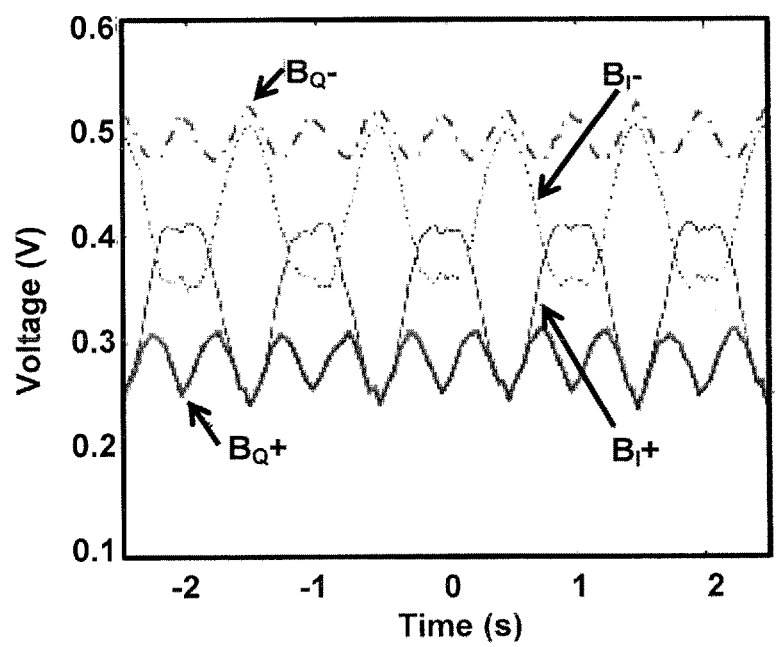

The final system configuration used in the following experiments is shown in FIG. 12, where the lightweight PCB was pasted to an upright piece of cardboard facing the target. A 0.15 m×0.15 m metal plate was attached to a Zaber T-LA60A-S actuator and placed at a distance (D) in front of the radar. FIG. 13 shows a 1-Hz vibration was used to test the I and Q baseband outputs, which are sampled by an oscilloscope. The experiment verifies the proper functionality of the differential I channels ($B_I+$, $B_I-$) and Q channels ($Q_I+$, $Q_I-$) at optimal and null detection point, as depicted in FIG. 1. The total power consumption of the radar chip including IF and baseband circuits is 377 mW at 1.2-V power supply.

Further test results on vibration and heartbeat detections were presented in [16]. The experimental results show that a small vibration displacement of 20 μm can be detected at D=0.3 m, and D reaches 2 m as the displacement increases to 0.2 mm. In the heartbeat detection, random body movement often results in the transition between optimal and null detection points every λ/8 (≈0.6 mm) in D. The quadrature outputs with CSD proved to ensure the robust detection.

C. Respiration Detection

Figure 14A:
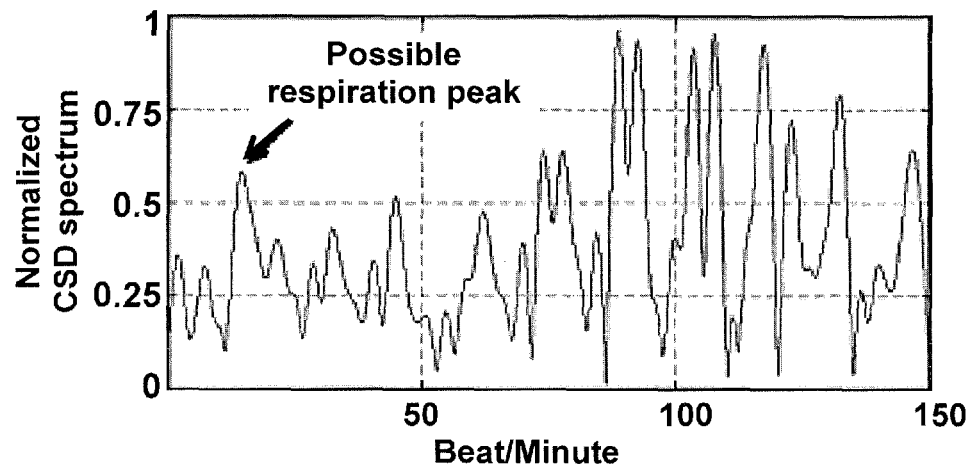
FIGS. 14A and 14B show respiration detection with two different $m_r$ showing (FIG. 14A) possible respiration peak at 15 beat/minute and (FIG. 14B) no prominent respiration peak.
Figure 14B:
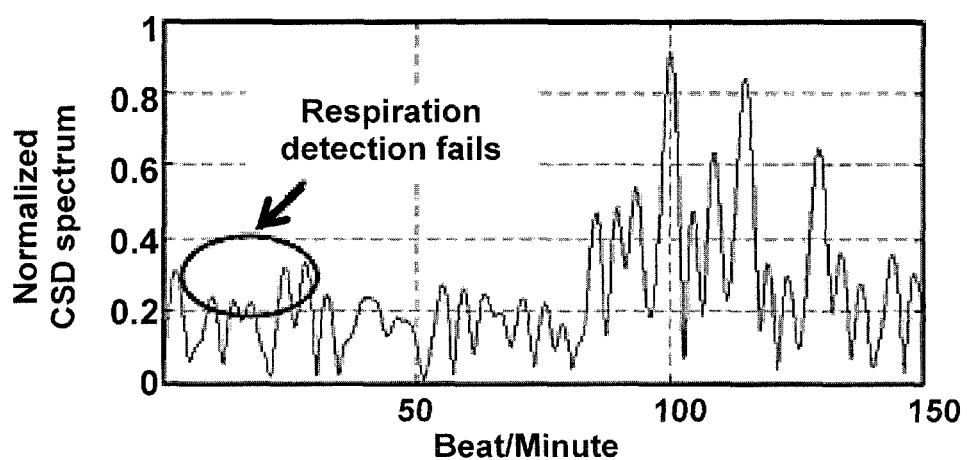

The chest-wall movement is modeled as $x(t)=m_r\cdot\sin(2\pi f_r t)+m_h\cdot\sin(2\pi f_h t)$, where $f_r$ and $f_h$ denote the frequency of respiration and heartbeat. As $m_r$ is comparable to or larger than λ, such as at least 0.9, at least 0.95, at least 0.96, at least 0.97, at least 0.98, at least 0.99, and/or at least 1 time λ, the modulated phase 4πx(t)/λ, in Equation 1A travels through multiples of 2π, and is no longer monotonic during inhale or exhale. This shows on the spectrum as harmonics and intermodulation, which seriously degrades the detection accuracy. FIGS. 14A and 14B shows the detection results of two different $m_r$ when $f_r$=15 beat/minute and D=0.3 m. FIG. 14A shows a possible respiration peak at around 15 beat/minute; however, many other peaks with large magnitude make the detection result in doubt. In some other cases, as $m_r$ changes, the main respiration peak is overwhelmed, and the respiration detection fails as shown in FIG. 14B.

To analyze this phenomenon, I channel output $B_I(t)$ can be modified from Equation 1A as x(t) is the chest-wall movement as $$B_I(t) \approx \cos\left\{\frac{4\pi[m_r\sin(2\pi f_r t) + m_h\sin(2\pi f_h t)]}{\lambda} + \phi_t\right\}. \quad (6)$$

Figure 15:
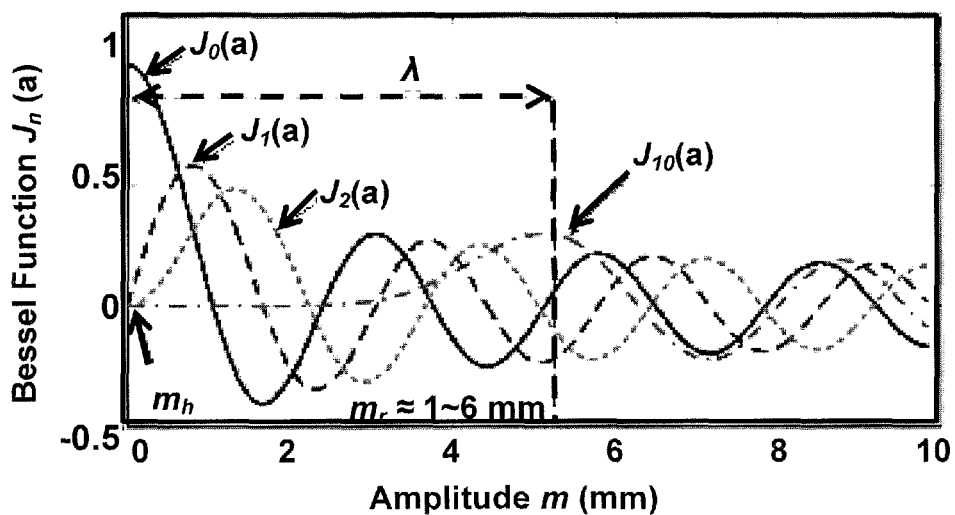
FIG. 15 shows $J_n(a)=J_n(4\pi m/\lambda)$ at 55 GHz versus vibration amplitude m.

Using the nth-order Bessel function of the first kind $J_n$, S(t) generated in CSD process can be represented by the summation of its frequency components [6] as $$S(t) = B_I(t) + jB_Q(t) \quad (7)$$

$$= \sum_{k=-\infty}^{\infty}\sum_{p=-\infty}^{\infty} J_k(a_r)\cdot J_p(a_h)\cdot$$

$$\exp[j\cdot 2\pi(kf_r + pf_h)t]\cdot\exp(\phi_t)$$

where $a_r=4\pi m_r/\lambda$ and $a_h=4\pi m_h/\lambda$. As FFT is applied on S(t) to obtain CSD spectrum, $\exp(\phi_t)$ has a constant magnitude and no longer affects the detection. A frequency component at x Hz is proportional to the sum of products [6]

$$H_x = \left|\sum_{k=-\infty}^{\infty}\sum_{p=\frac{(x-f_r h)}{f_h}}^{\infty} J_k(a_r)\cdot J_p(a_h)\right| \quad (8)$$

where $x=k\cdot f_r+p\cdot f_h$, and k and p are integers. In 5-GHz systems as m≪λ, the infinite sum can be approximated by only considering low orders of $J_n(a)$ (n=0, ±1) [6], and thus the output spectrum does not show prominent higher order harmonics. At 55 GHz, however, m is comparable to κ, and $H_x$ magnitudes formed by high orders of are no longer negligible, as seen in FIG. 15. For example, even for n=10, the harmonic associated with $J_{10}(a_r)$ is possibly present on the spectrum when m≈5 mm. In addition, the desired respiration tone is $H_{fr}=J_1(a_r)\cdot J_0(a_h)$ as k=1 and p=0. For typical respiration ($m_r\approx$1-6 mm), the value of $J_1(a_r)$ has several zero-crossing points, possibly resulting in an indistinguishable respiration peak such as FIG. 14B.

D. Time-Domain Recovery Algorithm

The above experiments at 55 GHz show the demodulation solely based on the recognition of peaks in frequency domain is susceptible to system nonlinearity and noise. To solve the detection difficulty when target displacement is comparable to or larger than λ, FIG. 16A illustrates the nonlinear input-output mapping in time domain. Two types of peaks (transition between positive and negative slope)

B(t) on can be identified. Type-I peaks (A and B) are due to the distortion of nonlinear system mapping, and Type-II peak (C) is corresponding to the real target displacement. Plotting both I and Q channels in FIG. 16B, the following relations can be found.

1) As a Type-I peak happens on $B_I(t)$, the sign of slope on $B_Q(t)$ remains unchanged (and vice versa).

2) As a Type-II peak happens, the sign of slope on $B_I(t)$ and $B_Q(t)$ change simultaneously. This indicates that the peak is due to the original displacement.

3) For any adjacent Type-I peaks (peak A and B) on $B_I(t)$, the corresponding sign of slope on $B_Q(t)$ is opposite (and vice versa).

Figure 17A:
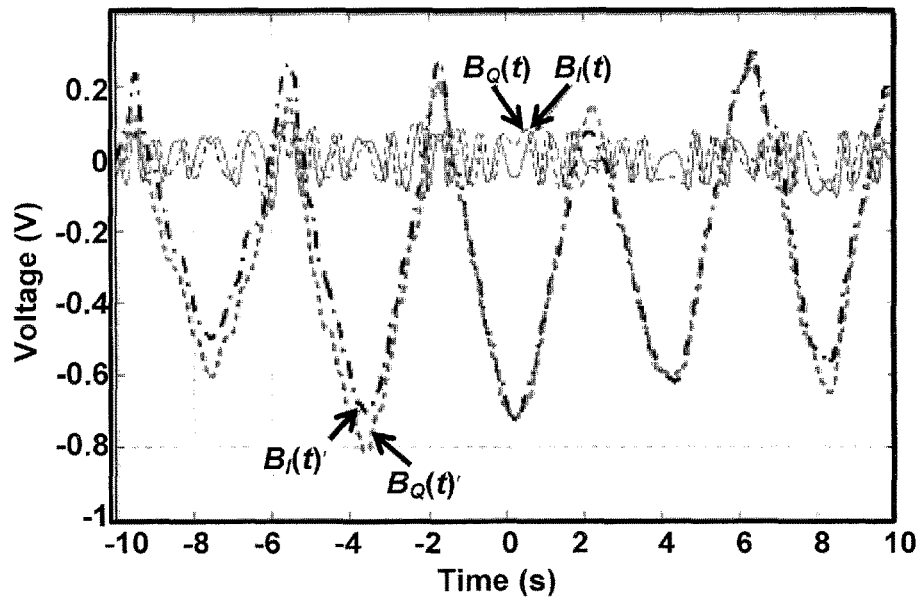
FIG. 17A shows respiration signals before and after an embodiment of a recovery algorithm in accordance with an embodiment of the invention is applied.
Figure 17B:
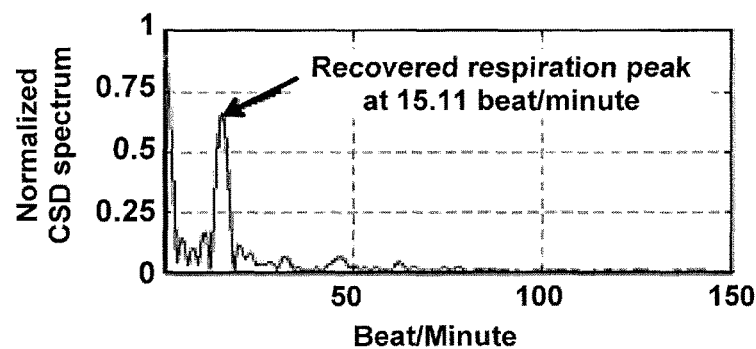
FIG. 17B shows a recovered respiration peak compared with that of FIG. 14B.

By cross referencing the outputs from I and Q channels, the algorithm is able to distinguish between Type-I and Type-II peaks. The ambiguity is resolved by the technique because at a fixed D, the system nonlinearity (Type-I peak) does not happen on both I and Q channels simultaneously due to the 90° phase difference. The algorithm preserves the nondistorted portion of the waveform (Follow mode) and recovers the distorted portion (Flip mode), as demonstrated in FIG. 16B. In FIG. 17A, the algorithm was applied on the baseband outputs $B_I(t)$ and $B_Q(t)$ of FIG. 14B, and the respiration movement was recovered on both $B_I(t)'$ and $B_Q(t)'$. The recovered CSD spectrum in FIG. 17B shows the accurate recovered respiration peak at 15.11 beat/minute.

The time-domain operation can be used to recover arbitrary respiration pattern which is different from the pure sinusoidal waveform modeled in Equation (6). A respiration example with inhalation for 2 s, exhalation for 2 s, and interval of 3 s was used in the test. The rate is $1/(2+2+3) \times 60 = 8.57$ beat/minute. FIG. 18A shows the respiration waveforms before applying the algorithm ($B_I(t)$ and $B_Q(t)$) and after applying the algorithm ($B_I(t)'$ and $B_Q(t)'$). Compared with FIG. 18B, where there is an ambiguous peak at 6.6 beats/minute, the correct respiration rate is recovered in FIG. 18C. As discussed in Sections I and IV-B, simultaneous detection of respiration and heartbeat proves to be difficult at 60 GHz; however, the experiment shows the possibility of detecting the heartbeat during any short interval (2 to 3 s) between breaths, especially for slow breathing during sleep. As shown in FIG. 18A, the algorithm is able to indicate the intervals during which the heartbeat can be detected, by successive Follow modes, in which the modulated phase of Equation 1A is less than $\pi$ and there is no large target displacement. Calculating the spectrum of this period (in dashed circle), heartbeat at 72 beat/minute is obtained in FIG. 18D, which is fairly close to the reference.

Aspects of the invention, such as controlling, transmitting, controlling receiving, and processing the radar signals, may be described in the general context of computer-executable instructions, such as program modules, being executed by a computer. Generally, program modules include routines, programs, objects, components, data structures, etc., that perform particular tasks or implement particular abstract data types. Moreover, those skilled in the art will appreciate that the invention may be practiced with a variety of computer-system configurations, including multiprocessor systems, microprocessor-based or programmable-consumer electronics, minicomputers, mainframe computers, and the like. Any number of computer-systems and computer networks are acceptable for use with the present invention.

Specific hardware devices, programming languages, components, processes, protocols, and numerous details including operating environments and the like are set forth to provide a thorough understanding of the present invention. In other instances, structures, devices, and processes are shown in block-diagram form, rather than in detail, to avoid obscuring the present invention. But an ordinary-skilled artisan would understand that the present invention may be practiced without these specific details. Computer systems, servers, work stations, and other machines may be connected to one another across a communication medium including, for example, a network or networks.

As one skilled in the art will appreciate, embodiments of the present invention may be embodied as, among other things: a method, system, or computer-program product. Accordingly, the embodiments may take the form of a hardware embodiment, a software embodiment, or an embodiment combining software and hardware. In an embodiment, the present invention takes the form of a computer-program product that includes computer-useable instructions embodied on one or more computer-readable media.

Computer-readable media include both volatile and non-volatile media, transitory and non-transitory, transient and non-transient media, removable and nonremovable media, and contemplate media readable by a database, a switch, and various other network devices. By way of example, and not limitation, computer-readable media comprise media implemented in any method or technology for storing information. Examples of stored information include computer-useable instructions, data structures, program modules, and other data representations. Media examples include, but are not limited to, information-delivery media, RAM, ROM, EEPROM, flash memory or other memory technology, CD-ROM, digital versatile disks (DVD), holographic media or other optical disk storage, magnetic cassettes, magnetic tape, magnetic disk storage, and other magnetic storage devices. These technologies can store data momentarily, temporarily, or permanently.

The invention may be practiced in distributed-computing environments where tasks are performed by remote-processing devices that are linked through a communications network. In a distributed-computing environment, program modules may be located in both local and remote computer-storage media including memory storage devices. The computer-useable instructions form an interface to allow a computer to react according to a source of input. The instructions cooperate with other code segments to initiate a variety of tasks in response to data received in conjunction with the source of the received data.

The present invention may be practiced in a network environment such as a communications network. Such networks are widely used to connect various types of network elements, such as routers, servers, gateways, and so forth. Further, the invention may be practiced in a multi-network environment having various, connected public and/or private networks.

Communication between network elements may be wireless or wireline (wired). As will be appreciated by those skilled in the art, communication networks may take several different forms and may use several different communication protocols. And the present invention is not limited by the forms and communication protocols described herein.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

REFERENCES

[1] C. Li, Y. Xiao, and J. Lin, "Experiment and spectral analysis of a low-power-band heartbeat detector measuring from four sides of a human body," *IEEE Trans. Microw. Theory Tech.*, vol. 54, no. 12, pp. 4465-4471, December 2006.

[2] A. D. Droitcour, O. Boric-Lubecke, V. M. Lubecke, J. Lin, and G. T. A. Kovac, "Range correlation and I/Q performance benefits in single-chip silicon Doppler radars for noncontact cardiopulmonary monitoring," *IEEE Trans. Microw. Theory Tech.*, vol. 52, no. 3, pp. 838-848, March 2004.

[3] C. Li, X. Yu, C. Lee, L. Ran, and J. Lin, "High-sensitivity software configurable 5.8 GHz radar sensor receiver chip in 0.13 μm CMOS for noncontact vital sign detection," *IEEE Trans. Microw. Theory Tech.*, vol. 58, no. 5, pp. 1410-1419, May 2010.

[4] E. Laskin, M. Khanpour, S. T. Nicolson, A. Tomkins, P. Garcia, A. Cathelin, D. Belot, and S. P. Voinigescu, "Nanoscale CMOS transceiver design in the 90-170 GHz range," *IEEE Trans. Microw. Theory Tech.*, vol. 57, no. 12, pp. 3477-3490, December 2009.

[5] S. Kim and C. Nguyen, "On the development of a multifunction millimeter-wave sensor for displacement sensing and low-velocity measurement," *IEEE Trans. Microw. Theory Tech.*, vol. 52, no. 52, pp. 2503-2512, November 2004.

[6] Y. Yan, L. Cattafesta, C. Li, and J. Lin, "Analysis of detection methods and realization of a real-time monitoring RF vibrometer," *IEEE Trans. Microw. Theory Tech.*, vol. 59, no. 12, pp. 3556-3566, December 2011.

[7] C. Li and J. Lin, "Complex signal demodulation and random body movement cancellation techniques for noncontact vital sign detection," in *IEEE MTT-S Int. Microw. Symp. Dig.*, June 2008, pp. 567-570.

[8] D. T. Petkie, C. Benton, and E. Bryan, "Millimeter wave radar for remote measurement of vital signs," in *Proc. IEEE Radar Conf.*, May 2009, pp. 1-3.

[9] E. Knott, *Radar Handbook*. New York, N.Y., USA: McGraw-Hill, 2008, ch. 14, p. 10.

[10] S. Reynolds, B. Floyd, U. Pfeiffer, T. Beukema, J. Grzyb, C. Haymes, B. Gaucher, and M. Soyuer, "A sillicon 60 GHz receiver and transmitter chipset for broadband communications," *IEEE J. Solid-State Circuits*, vol. 41, no. 12, pp. 2820-2831, December

[11] J. Lee, Y. Chen, and Y. Huang, "A low-power low-cost fully-integrated 60-GHz transceiver system with OOK modulation and on-board antenna assembly," *IEEE J. Solid-State Circuits*, vol. 45, no. 2, pp. 264-275, February 2010.

[12] A. Jentzsch and W. Heinrich, "Theory and measurements of flip-chip interconnects for frequencies up to 100 GHz," *IEEE Trans. Microw. Theory Tech.*, vol. 49, no. 5, pp. 871-878, May 2001.

[13] C.-C. Kuo, P.-A. Lin, C.-F. Tai, Y.-L. Chang, Y.-S. Jiang, J.-H. Tsai, H.-C. Lu, Y.-M. Hsin, and H. Wang, "Flip chip assembled W-band CMOS chip modules on ceramic substrate with transition compensation for millimeter-wave system-in-package integration," *IEEE Trans. Microw. Theory Tech.*, vol. 60, no. 3, pp. 766-777, March 2012.

[14] C. Li and J. Lin, "Optimal carrier frequency of noncontact vital sign detectors," in *Proc. IEEE Radio Wireless Symp.*, January 2007, pp. 281-284.

[15] H. Chuang, H. Kuo, F. Lin, T. Huang, C. Kuo, and Y. Ou, "60-GHz millimeter-wave life detection system (MLDS) for noncontact human vital-signal monitoring," *IEEE Sensors J.*, vol. 12, no. 3, pp. 602-609, March 2012.

[16] T.-Y. J. Kao, A. Y.-K. Chen, Y. Yan, T. Shen, and J. Lin, "Aflip-chip-packaged and fully-integrated 60 GHz CMOS micro-radar sensor for heartbeat and mechanical vibration detections," in *Proc. IEEE Radio Frequency Integr. Circuits Symp.*, June 2012, pp. 443-446.

[17] T. Yao, M. Q. Gordon, K. K. W. Tang, K. H. K. Yau, M. Yang, P. Schvan, and S. P. Voinigescu, "Algorithmic design of CMOS LNAs and PAs for 60 GHz radio," *IEEE J. Solid-State Circuits*, vol. 42, no. 5, pp. 1044-1057, May 2007.

[18] S. Pellerano, Y. Palaskas, and K. Soumyanath, "A 64 GHz LNA with 15.5 gain and 6.5 dB NF in 90 nm CMOS," *IEEE J. Solid-State Circuits*, vol. 43, no. 7, pp. 1542-1552, July 2008.

[19] J. L. Kuo, Z. M. Tsai, K. Y. Lin, and H. Wang, "A 50 to 70 GHz power amplifier using 90 nm CMOS technology," *IEEE Microw, Wireless Compon. Lett.*, vol. 19, no. 1, pp. 45-47, January 2009.

[20] M. Kraemer, D. Dragomirescu, and R. Plana, "Accurate electromagnetic simulation and measurement of millimeter-wave inductors in bulk CMOS technology," in *Proc. 10th Top. Meeting Silicon Monolithic Integr. Circuits RF Syst.*, January 2010, pp. 61-64.

[21] T. O. Diskson, M. A. LaCroix, S. Boret, D. Gloria, R. Beekens, and S. P. Voinigescu, "30-100 GHz inductors and transformers for millimeter-wave (Bi) CMOS integrated circuits," *IEEE Trans. Microw. Theory Tech.*, vol. 53, no. 1, pp. 123-134, January 2005.

[22] Y. Cao, R. A. Groves, X. Huang, N. D. Zamdmer, J. O. Plouchart, R. A. Wachnik, T. J. King, and C. Hu, "Frequency-independent equivalent circuit model for on-chip spiral inductors," *IEEE J. Solid-State Circuits*, vol. 38, no. 3, pp. 419-426, March 2003.

[23] C. K. Liang and B. Razavi, "Systematic transistor and inductor modeling for millimeter-wave design," *IEEE J. Solid-State Circuits*, vol. 44, no. 2, pp. 450-457, February 2009.

[24] C. Cao and K. K. O., "Millimeter-wave voltage-controlled oscillators in 0.13-m CMOS technology," *IEEE J. Solid-State Circuits*, vol. 41, no. 6, pp. 1297-1304, June 2006.

[25] W. Yan and H. Luong, "A 900-MHz CMOS low-phase-noise voltage-controlled ring oscillator," *IEEE Trans. Circuits Syst. II, Analog Dig. Signal Process.*, vol. 48, no. 2, pp. 216-221, February 2001.

APPENDIX
MATLAB® CODING OF TIME-DOMAIN RECOVERY ALGORITHM

```
clc; clear all; close all;

Data = csvread('C:\Users\Jason\Desktop\Measurement\Full_system_0308\scope_255.csv',2,0);

fs = 1/(Data(2,1) - Data(1,1))    %Extract sampling frequency fs.
%----------------------------------------------------------------
% Remove dc component. Q_p and I_p: positive baseband outputs of the Q
% and I channels. Q_m and I_m:
% negtive baseband outputs of the Q and I channels.

Q_p = Data(:,2)-mean(Data(:,2));
Q_m = Data(:,3)-mean(Data(:,3));
I_p = Data(:,4)-mean(Data(:,4));
I_m = Data(:,5)-mean(Data(:,5));

Q_p_raw = Q_p;    %Store the raw data for later comparison.
I_p_raw = I_p;

%----------------------------------------------------------------
% Choose to turn on or off the 3 levels of data smoothing. The simple
% moving average acts like a low-pass filter to reduce the effect of noise
% and prevent the misjudgment of recovery algorithm. Depending on the
% quality of raw data, more filters can be turned on to improve the
% recovery accuracy.

for i = 2:length(I_p)-1           % Low-pass filter for I_p
    I_p(i) = ( I_p(i-1)+I_p(i+1) )/2;
end
for i = 2:length(I_p)-1
    I_p(i) = ( I_p(i-1)+I_p(i+1) )/2;
end
for i = 2:length(I_p)-1
    I_p(i) = ( I_p(i-1)+I_p(i+1) )/2;
end for i = 2:length(Q_p)-1           % Low-pass filter for Q_p
    Q_p(i) = ( Q_p(i-1)+Q_p(i+1) )/2;
end for i = 2:length(Q_p)-1
    Q_p(i) = ( Q_p(i-1)+Q_p(i+1) )/2;
end for i = 2:length(Q_p)-1
    Q_p(i) = ( Q_p(i-1)+Q_p(i+1) )/2;
end
%----------------------------------------------------------------
figure
plot(Data(:,1), I_p, '-r');  % Plot I_p before the recovery algorithm
hold on;
```

```
h_axis=gca;
get(h_axis,'FontSize'); % displays the default Font size
set(h_axis,'FontSize',16); % sets the font size of axis
AX = legend('B_I(t)');
LEG = findobj(AX,'type','text');
set(LEG,'FontSize',16)
grid;
ylabel('Voltage(V)');
h_ylabel = get(gca,'YLabel');
set(h_ylabel,'FontSize',16);
xlabel('Time(s)');
h_xlabel = get(gca,'XLabel');
set(h_xlabel,'FontSize',16);
title('Time-domain Vital Sign Recovery');
h = get(gca, 'title');
set(h, 'FontSize', 16);

plot(Data(:,1), Q_p, '-b'); % Plot Q_p before the recovery algorithm

% ----------------------------------------------------------------
% Find the trend of I_p and Q_p signal and save the value to Trd_Ip and
% Trd_Qp. 1 represents the voltage level is rising, and 0 represents the
% voltage level is falling.

Trd_Ip(1) = 1;   %Assign arbitrary trend to the first index
for i = 2:length(I_p)
    if I_p(i) > I_p(i-1)
        Trd_Ip(i) = 1;
    elseif I_p(i) < I_p(i-1)
        Trd_Ip(i) = 0;
    else
        Trd_Ip(i) = ~Trd_Ip(i-1);   %If I_p(i) = I_p(i-1), inverse Trd_Ip
                                    %to prevent a false trend. It
                                    %eliminates the slope = 0 case.
    end
end
Trd_Qp(1) = 1;   %Assign arbitrary trend to the first one
for i = 2:length(Q_p)
    if Q_p(i) > Q_p(i-1)
        Trd_Qp(i) = 1;
    elseif Q_p(i) < Q_p(i-1)
        Trd_Qp(i) = 0;
    else
        Trd_Qp(i) = ~Trd_Qp(i-1);   %If Q_p(i) = Q_p(i-1), inverse Trd_Qp
                                    %to prevent a false trend. It
                                    %eliminates the slope = 0 case.
    end
end % ----------------------------------------------------------------
% Start of the recovery process.
% I_p_fix and Q_p_fix represent the signal after recovery. Initially
% I_p_fix = I_p and Q_p_fix = Q_p;
```

```
I_p_fix = I_p;
Q_p_fix = Q_p;

% IF flip == 1, it is in flip status. IF flip == 0, it is in follow status.
% Initially set flip = 1.

flip_I = 1;
flip_Q = 1;

% Assign arbitrary initial value to previos peak and slope type as long as
% they are not equal to the value 0, 1, and -1.

PT_I_Last = 10;
Sp_Q_Last = 10;
PT_Q_Last = 10;
Sp_I_Last = 10;
for i = 4:length(Trd_Ip)-3
    [PC_I PT_I] = PeakCheck(Trd_Ip, i, 1);   % Check if there is a valid
                                              % peak on I_p.
    [TC_Q Sp_Q] = TrendCheck(Trd_Qp, i, 1);  % Check if there is a
                                              % consistent trend on Q_p
                                              % If yes, a Type-I peak is
                                              % identified on I_p.
    if PC_I && TC_Q && (Sp_Q_Last ~= Sp_Q)
            flip_I = ~flip_I;   % Switch flip to follow stage or follow
                                % to flip stage.
            if flip_I == 1
                I_p_fix(i:end) = I_p_fix(i:end) - 2*(I_p(i) - I_p(i-
1))*ones(length(I_p(i:end)),1);   %Flipping I_p and store the data to I_p_fix
            end
        PT_I_Last = PT_I;   %Store the current peak and sloep type.
        Sp_Q_Last = Sp_Q;
    else
        if flip_I == 1
            I_p_fix(i:end) = I_p_fix(i:end) - 2*(I_p(i) - I_p(i-
1))*ones(length(I_p(i:end)),1);
        end
    end

[PC_Q PT_Q] = PeakCheck(Trd_Qp, i, 1);   % Check if there is a valid
                                              % peak on Q_p.
    [TC_I Sp_I] = TrendCheck(Trd_Ip, i, 1);  % Check if there is a
                                              % consistent trend on I_p
                                              % If yes, a Type-I peak is
                                              % identified on Q_p
    if PC_Q && TC_I && (Sp_I_Last ~= Sp_I)
            flip_Q = ~flip_Q;   % Switch flip to follow stage or follow
                                % to flip stage.
            if flip_Q == 1
                Q_p_fix(i:end) = Q_p_fix(i:end) - 2*(Q_p(i) - Q_p(i-
1))*ones(length(Q_p(i:end)),1);   %Flipping Q_p and store the data to Q_p_fix.
```

```
            end
        PT_Q_Last = PT_Q;    %Store the current peak and sloep type.
        Sp_I_Last = Sp_I;
    else
        if flip_Q == 1
            Q_p_fix(i:end) = Q_p_fix(i:end) - 2*(Q_p(i) - Q_p(i-
1))*ones(length(Q_p(i:end)),1);
        end
    end
end
plot(Data(:,1), I_p_fix, '-k');  %Plot the recovered waveforms.
plot(Data(:,1), Q_p_fix, '-g');

AX = legend('B_I(t)','B_Q(t)','B_I(t)','B_Q(t)');
hold off;

% -----------------------------------------------------------------
% Start complex signal demodulation [5]

CSD1 = I_p_fix + j*Q_p_fix;  % Recovered data
CSD3 = I_p_raw + j*Q_p_raw;  % Use raw data before the waveform smoothing.

L = 2^20;    %FFT number of point

[H1t, W1t] = dtft(CSD1, L);
    H1 = H1t(L/2+1:L);
    W1 = W1t(L/2+1:L);
[H3t, W3t] = dtft(CSD3, L);
    H3 = H3t(L/2+1:L);
    W3 = W3t(L/2+1:L);
%----------------------------------------------------------------- figure;
plot (W3/pi*(fs/2)*60, abs(H3),'-b');  % Plot the baseband spectrum before
                                        % recovery
h_axis=gca;
get(h_axis,'FontSize');  % displays the default Font size
set(h_axis,'FontSize',16);  % sets the font size of axis
xlim([0 150]);
grid;
ylabel('CSD Spectrum');
h_ylabel = get(gca,'YLabel');
set(h_ylabel,'FontSize',16);
xlabel('Beat/Minute');
h_xlabel = get(gca,'XLabel');
set(h_xlabel,'FontSize',16);
title('Baseband Spectrum Before Recovery');
h = get(gca, 'title');
set(h, 'FontSize', 16);
```

```
figure;
plot (W1/pi*(fs/2)*60, abs(H1),'-r'); % Plot the baseband spectrum after
                                      % recovery
h_axis=gca;
get(h_axis,'FontSize'); % displays the default Font size
set(h_axis,'FontSize',16); % sets the font size of axis
xlim([0 150]);
grid;
ylabel('CSD Spectrum');
h_ylabel = get(gca,'YLabel');
set(h_ylabel,'FontSize',16);
xlabel('Beat/Minute');
h_xlabel = get(gca,'XLabel');
set(h_xlabel,'FontSize',16);
title('Baseband Spectrum After Recovery');
h = get(gca, 'title');
set(h, 'FontSize', 16);

%----------------------------------------------------------------- function [PC PT] = PeakCheck(Trend, Idx, N)
% Idx: center index,
% Centered at Idx, check N indexes to the left and N-1 to the right to
% determine if it is a valid peak. N>=1.
% If it is a valid peak, PC==1. If it is not a valid peak, PC==0.
% If the peak type is rising first and then falling, PT == 1.
% If the peak type is falling first and then rising, PT == 0.

PC = 0;
PT = 0;
i = 1;
while i <= N
        if (Trend(Idx) == Trend(Idx+i-1)) && (Trend(Idx) ~= Trend(Idx-i))
            if i == N
                PC = 1;
                if Trend(Idx+i-1) == 0
                    PT = 1;
                else
                    PT = 0;
                end
            end
            i = i+1;
        else
            PC = 0; break
        end
end
```

```
%------------------------------------------------------------------------ function [TC Sp]= TrendCheck(Trend, Idx, N)
% Idx: center index,
% Centered at Idx, check N indexes to the left and N-1 indexes to the right
% to determine if there is a consistent trend. N>=1.
% If there is a consistent trend, TC == 1. If there is not a consistent
% trend, TC == 0.
% If the slope of the trend > 0, Sp == 1. If the slope of the trend < 0,
% then Sp == -1.

% The generate of trend functions Trd_Ip and Trd_Qp has eliminated the
% slope = 0 case.

TC = 1;
i = Idx-N+1;
while (TC == 1) && (i <= Idx+N-1)
    if Trend(Idx-N) == Trend(i)
        TC = 1;
        if Trend(i) == 1
            Sp = 1;
        else
            Sp = -1;
        end
        i = i+1;
    else
        TC = 0;
        Sp = 0;
        break
    end
end

%------------------------------------------------------------------------ function [H, W] = dtft(h, N)
%DTFT   calculate DTFT at N equally spaced frequencies
%-----
%  Usage:    [H, W] = dtft(h, N)
%
%     h : finite-length input vector, whose length is L
%     N : number of frequencies for evaluation over [-pi,pi)
%         ==> constraint: N >= L
%     H : DTFT values (complex)
%     W : (2nd output) vector of freqs where DTFT is computed
%

%---------------------------------------------------------------
% copyright 1994, by C.S. Burrus, J.H. McClellan, A.V. Oppenheim,
% T.W. Parks, R.W. Schafer, & H.W. Schussler.  For use with the book
% "Computer-Based Exercises for Signal Processing Using MATLAB"
% (Prentice-Hall, 1994).
%---------------------------------------------------------------
```

```
N = fix(N);
L = length(h);  h = h(:);  %<-- for vectors ONLY !!!
if( N < L )
   error('DTFT: # data samples cannot exceed # freq samples')
end
W = (2*pi/N) * [ 0:(N-1) ]';
mid = ceil(N/2) + 1;
W(mid:N) = W(mid:N) - 2*pi;   % <--- move [pi,2pi) to [-pi,0)
W = fftshift(W);
H = fftshift( fft( h, N ) );  %<--- move
```

The invention claimed is:

1. A method of determining a vibration rate of a target, comprising:
    transmitting a transmit signal from a transmitting antenna of a radar transceiver at the target such that the transmit signal is reflected by the target to create a reflected signal, wherein the target has at least a first side and second side,
        wherein the transmit signal and the reflected signal are electromagnetic signals having a wavelength, $\lambda$, the transmit signal is directed to the first side of the target and the reflected signal is reflected by the first side of the target,
        where the transmit signal is represented as T(t)=cos (2πft+$\phi_{vco}$),
        wherein the reflected signal is based, at least in part, on a first vibration of the target having a first frequency, $f_r$, and a first amplitude, $m_r$, and a second vibration of the target having a second frequency, $f_h$, and a second amplitude, $m_h$;
    receiving the reflected signal via a receiving antenna of the radar transceiver to create a receive signal, where the receiving antenna, the transmitting antenna, at least one processing circuitry, and the radar transceiver are disposed on a common substrate;
    demodulating the receive signal by the at least one processing circuitry of the radar transceiver to produce a baseband output B(t),
    where $$B(t) \approx \cos\left(\frac{4\pi x(t)}{\lambda} + \phi_t\right),$$

where $\phi_t$ is a total accumulated residual phase, and x(t)=$m_r$ sin(2π$f_r$t)+$m_h$ sin(2π$f_h$t),
    where S(t)=$B_I$(t)+j$B_Q$(t),
    where $$B_I(t) \approx \cos\left\{\frac{4\pi x(t)}{\lambda} + \phi_t\right\} = \cos\left\{\frac{4\pi[m_r\sin(2\pi f_r t) + m_h\sin(2\pi f_h t)]}{\lambda} + \phi_t\right\}$$

$$B_Q(t) \approx \sin\left\{\frac{4\pi x(t)}{\lambda} + \phi_t\right\} = \sin\left\{\frac{4\pi[m_r\sin(2\pi f_r t) + m_h\sin(2\pi f_h t)]}{\lambda} + \phi_t\right\};$$

identifying, by the at least one processing circuitry, distorted portions of $B_I$(t) or distorted portions of $B_Q$(t), where the distorted portions of $B_I$(t) or the distorted portions of $B_Q$(t) are portions of $B_I$(t) or portions of $B_Q$(t) that are distorted by system nonlinearity, respectively;
    producing, by the at least one processing circuitry, recovered portions of $B_I$(t) or recovered portions of $B_Q$(t) that correspond to the distorted portions of $B_I$(t) or the distorted portions of $B_Q$(t), respectively;
    replacing, by the at least one processing circuitry, the distorted portions of $B_I$(t) or the distorted portions of $B_Q$(t) with the recovered portions of $B_I$(t) or the recovered portions of $B_Q$(t) to produce a recovered $B_I$(t) or a recovered $B_Q$(t), respectively;
    applying a Fourier transform, by the at least one processing circuitry, to S(t) to produce a frequency spectrum of S(t); and
    determining, by the at least one processing circuitry, the second frequency $f_h$ from the frequency spectrum of S(t).

2. The method according to claim 1, wherein identifying the distorted portions of $B_I$(t) or the distorted portions of $B_Q$(t) comprises:
    identifying peaks in $B_I$(t) or peaks in $B_Q$(t), where a peak is a location in $B_I$(t) or a location in $B_Q$(t) where a slope of $B_I$(t) or a slope of $B_Q$(t) changes sign from positive to negative or from negative to positive, respectively; and
    identifying whether each peak of the peaks in $B_I$(t) or the peaks in $B_Q$(t) is a type I peak, where a type I peak is the peak in $B_I$(t) that occurs when the sign of the slope of $B_Q$(t) remains unchanged or a peak in $B_Q$(t) that occurs when the sign of the slope of $B_I$(t) remains unchanged,
    wherein a distorted portion of $B_I$(t) or a distorted portion of $B_Q$(t) starts when $B_I$(t) or $B_Q$(t) is not in the distorted portion of $B_I$(t) or the distorted portion of $B_Q$(t) and a type I peak is identified in $B_I$(t) or $B_Q$(t), respectively,
    wherein the distorted portion of $B_I$(t) or the distorted portion of $B_Q$(t) ends when $B_I$(t) or $B_Q$(t) is in the distorted portion of $B_I$(t) or the distorted portion of $B_Q$(t) and a type I peak is identified in $B_I$(t) or $B_Q$(t), respectively.

3. The method according to claim 2, wherein producing the recovered portions of $B_I$(t) or the recovered portions of $B_Q$(t) comprises:
    flipping a direction of a magnitude change of a value of the distorted portions of $B_I$(t) or the distorted portions of $B_Q$(t) as compared with a preceding value of the distorted portions of $B_I$(t) or the distorted portions of $B_Q$(t) such that a value of the recovered portions of $B_I$(t) or the recovered portions of $B_Q$(t) is a preceding value of the recovered portions of $B_I$(t) or the recovered portions of $B_Q$(t) added together with a change in magnitude equal to the magnitude change in the distorted portions of $B_I$(t) or the distorted portions of $B_Q$(t) and having an opposite direction of magnitude change as the direction of magnitude change in the distorted portions of $B_I$(t) or the distorted portions of $B_Q$(t), respectively.

4. The method according to claim 1, further comprising:
    applying, by the processing circuitry, a Fourier transform to S(t) containing a portion of $B_I$(t) or a portion of $B_Q$(t) that is not within the distorted portion of $B_I$(t) or the distorted portion of $B_Q$(t), respectively, to produce a second frequency spectrum of S(t); and
    determining, by the processing circuitry, the second frequency $f_h$ from the second frequency spectrum of S(t).

5. The method according to claim 1, wherein the target is an animal and the first vibration is a front chest-wall movement of the animal and the second vibration is a heartbeat of the animal.

6. The method according to claim 5, wherein the animal is a human.

7. The method according to claim 6, wherein the first frequency $f_r$ is a respiration rate of the human.

8. The method according to claim 5, wherein the first amplitude $m_r$ and the first frequency $f_r$ are a magnitude of respiration and a frequency of respiration, respectively, and the second amplitude $m_h$ and the second frequency $f_h$ are a magnitude of heartbeat and a frequency of heartbeat, respectively.

9. The method according to claim 1, wherein the first amplitude $m_r$ is at least (0.9)$\lambda$.

10. The method according to claim 1, wherein the first amplitude $m_r$ is at least $\lambda$.

11. The method according to claim 1, wherein the first amplitude $m_r$ is greater than $\lambda$.

12. The method according to claim 1, wherein a frequency of the transmit signal is at least 55 GHz.

13. The method according to claim 6, wherein the first amplitude $m_h < (0.1) m_r$.

14. An apparatus, comprising:
a transmitter, wherein the transmitter is configured to transmit a transmit signal from a transmitting antenna of a radar transceiver at a target such that the transmit signal is reflected by the target to create a reflected signal, wherein the target has at least a first side and a second side,
  wherein the transmit signal and the reflected signal are electromagnetic signals having a wavelength, $\lambda$, the transmit signal is directed to the first side of the target and the reflected signal is reflected by the first side of the target,
  where the transmit signal is represented as $T(t)=\cos(2\pi f t + \phi_{vco})$,
  wherein the reflected signal is based, at least in part, on a first vibration having a first frequency, $f_r$, and a first amplitude, $m_r$, and a second vibration having a second frequency, $f_h$, and a second amplitude, $m_h$;
a receiver, wherein the receiver is configured to receive the reflected signal via a receiving antenna of the radar transceiver to create a receive signal, where the transmitting antenna and the receiving antenna are disposed on a common substrate;
demodulation circuitry disposed on the common substrate, wherein the demodulation circuitry is arranged to:
  demodulate the receive signal to produce a baseband output $B(t)$, where $$B(t) \approx \cos\left(\frac{4\pi x(t)}{\lambda} + \phi_t\right),$$

where $\phi_t$ is a total accumulated residual phase, and $x(t) = m_r \sin(2\pi f_r t) + m_h \sin(2\pi f_h t)$,
  where $S(t) = B_I(t) + j B_Q(t)$,
  where $$B_I(t) \approx \cos\left\{\frac{4\pi x(t)}{\lambda} + \phi_t\right\} = \cos\left\{\frac{4\pi[m_r\sin(2\pi f_r t) + m_h\sin(2\pi f_h t)]}{\lambda} + \phi_t\right\}$$

$$B_Q(t) \approx \sin\left\{\frac{4\pi x(t)}{\lambda} + \phi_t\right\} = \sin\left\{\frac{4\pi[m_r\sin(2\pi f_r t) + m_h\sin(2\pi f_h t)]}{\lambda} + \phi_t\right\};$$

and
processing circuitry disposed on the common substrate comprising a processor, the processing circuitry configured to:
  identify distorted portions of $B_I(t)$ or distorted portions of $B_Q(t)$, where the distorted portions of $B_I(t)$ or the distorted portions of $B_Q(t)$ are portions of $B_I(t)$ or portions of $B_Q(t)$ that are distorted by system non-linearity,
  produce recovered portions of $B_I(t)$ or recovered portions of $B_Q(t)$ that correspond to the distorted portions of $B_I(t)$ or the distorted portions of $B_Q(t)$, respectively,
  replace the distorted portions of $B_I(t)$ or the distorted portions of $B_Q(t)$ with the recovered portions of $B_I(t)$ or the recovered portions of $B_Q(t)$ to produce a recovered $B_I(t)$ or a recovered $B_Q(t)$, respectively,
  apply a Fourier transform, to $S(t)$ to produce a frequency spectrum of $S(t)$, and
  determine the second frequency $f_h$ from the frequency spectrum of $S(t)$.

15. The apparatus of claim 14, wherein the processing circuitry is further configured to identify the distorted portions of $B_I(t)$ or the distorted portions of $B_Q(t)$ via the processor:
  identifying peaks in $B_I(t)$ or peaks in $B_Q(t)$ where a peak is a location on $B_I(t)$ or $B_Q(t)$ where a slope of $B_I(t)$ or a slope of $B_Q(t)$ changes sign from positive to negative or from negative to positive; and
  identifying whether each peak of the peaks in $B_I(t)$ or the peaks in $B_Q(t)$ is a type I peak, where the type I peak is a peak in $B_I(t)$ that occurs when the sign of the slope of $B_Q(t)$ remains unchanged or a peak in $B_Q(t)$ that occurs when the sign of the slope of $B_I(t)$ remains unchanged,
  wherein the distorted portion of $B_I(t)$ or the distorted portion of $B_Q(t)$ starts when $B_I(t)$ or $B_Q(t)$ is not in the distorted portion of $B_I(t)$ or the distorted portion of $B_Q(t)$ and a type I peak is identified in $B_I(t)$ or $B_Q(t)$, respectively,
    wherein the distorted portion of $B_I(t)$ or the distorted portion of $B_Q(t)$ ends when $B_I(t)$ or $B_Q(t)$ is in a distorted portion of $B_I(t)$ or a distorted portion of $B_Q(t)$ and a type I peak is identified in Mt) or $B_Q(t)$, respectively,
  wherein the processor is configured to produce the recovered portions of $B_I(t)$ or the recovered portions of $B_Q(t)$ via the processor flipping a direction of a magnitude change of a value of the distorted portions of $B_I(t)$ or the distorted portions of $B_Q(t)$ as compared with a preceding value of the distorted portions of $B_I(t)$ or the distorted portions of $B_Q(t)$ such that a value of the recovered portions of $B_I(t)$ or the recovered portions of $B_Q(t)$ is a preceding value the recovered portions of $B_I(t)$ or the recovered portions of $B_Q(t)$ added together with a change in magnitude equal to the magnitude change in the distorted portions of $B_I(t)$ or the distorted portions of $B_Q(t)$ having an opposite direction of change in value as the direction of the magnitude change in the distorted portions of $B_I(t)$ or the distorted portions of $B_Q(t)$, respectively.

16. The apparatus of claim 14, wherein the processing circuitry is further configured to:
  apply a Fourier transform to $S(t)$ containing a portion of $B_I(t)$ or a portion of $B_Q(t)$ that is not within the distorted portion of $B_I(t)$ or the distorted portion of $B_Q(t)$ to produce a second frequency spectrum of $S(t)$; and
  determine the second frequency $f_h$ from the second frequency spectrum of $S(t)$.

* * * * *